United States Patent
Weinmann et al.

(10) Patent No.: US 6,245,828 B1
(45) Date of Patent: Jun. 12, 2001

(54) POLYMERIZABLE COMPOSITIONS BASED ON EPOXIDES

(75) Inventors: Wolfgang Weinmann, Herrsching; Oswald Gasser, Seefeld; Rainer Guggenberger, Herrsching; Gunther Lechner, Worthsee; Wolfgang Soglowek, Herrsching; Joachim Zech, Hechendorf, all of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/101,867

(22) PCT Filed: Nov. 21, 1997

(86) PCT No.: PCT/EP97/06504

§ 371 Date: Sep. 21, 1998

§ 102(e) Date: Sep. 21, 1998

(87) PCT Pub. No.: WO98/22521

PCT Pub. Date: May 28, 1998

(30) Foreign Application Priority Data

Nov. 21, 1996 (DE) .............................. 196 48 283

(51) Int. Cl.$^7$ .................... A61K 6/087; C08L 63/00; C08G 59/24; C08G 59/32

(52) U.S. Cl. .................... 522/148; 522/83; 522/170; 523/116; 523/427; 523/428; 523/433; 525/524; 525/525; 525/526; 528/33; 528/37; 528/40; 528/418; 549/32; 549/215; 549/463; 549/547; 433/228.1

(58) Field of Search ................... 522/170, 83, 148; 523/116, 427, 428, 433; 549/32, 215, 463, 547; 528/33, 37, 40, 418; 433/228.1

(56) References Cited

U.S. PATENT DOCUMENTS

| | | |
|---|---|---|
| 3,449,274 * | 6/1969 | Salensky . |
| 3,956,317 * | 5/1976 | Batzer . |
| 4,279,717 | 7/1981 | Eckberg et al. . |
| 4,576,999 | 3/1986 | Eckberg . |
| 5,260,349 * | 11/1993 | Crivello . |
| 5,556,896 | 9/1996 | Byerley et al. . |

FOREIGN PATENT DOCUMENTS

| | | |
|---|---|---|
| 3038153A1 | 6/1982 | (DE) . |
| 4133494A1 | 4/1993 | (DE) . |
| 4324322A1 | 1/1995 | (DE) . |
| 4405148C1 | 5/1995 | (DE) . |
| 4421623A1 | 1/1996 | (DE) . |
| 19534668A1 | 3/1997 | (DE) . |
| 03810096 | 8/1990 | (EP) . |
| 20394192 | 10/1990 | (EP) . |
| 0434010A1 | 6/1991 | (EP) . |
| 0524524A1 | 1/1993 | (EP) . |
| 0532896A2 | 3/1993 | (EP) . |
| 0748831A2 | 12/1996 | (EP) . |
| 9530402 | 11/1995 | (WO) . |
| 9613538 | 5/1996 | (WO) . |

* cited by examiner

Primary Examiner—David J. Buttner
(74) Attorney, Agent, or Firm—Birch, Stewart, Kolasch & Birch, LLP

(57) ABSTRACT

The present invention is directed to polymerizable dental compositions containing a) 3 to 80 wt. % of cycloaliphatic epoxides; b) 0 to 80 wt. % of an epoxide or a mixture of epoxides which are different from a); c) 3 to 85 wt. % of a filler material; d) 0.01 to 25 wt. % of initiators, inhibitors and/or accelerators; e) 0 to 25 wt. % of auxiliary agents, the individual percentages of which are in relation to the total weight. The new polymerizable agents are particularly suited as dental material.

11 Claims, No Drawings

POLYMERIZABLE COMPOSITIONS BASED ON EPOXIDES

This application is the national phase under 35 U.S.C. §371 of prior PCT International Application No., PCT/EP97/06504, which has an International filing date of Nov. 21, 1997, which designated the United States of America, the entire contents of which are hereby incorporated by reference.

The invention relates to polymerizable compositions based on epoxides, new cycloaliphatic epoxides and their use.

Methacrylate and acrylate monomers have hitherto chiefly been used in polymerizable dental compositions. 2,2-Bis[4,1-phenylenoxy(2-hydroxy-3,1-propanediyl)-methacrylic acid ester]-propylidene (bis-GMA) [U.S. Pat. No. 3,066,112], described by Bowen, deserves particular attention. Mixtures of this methacrylate with triethylene glycol dimethacrylate are also used nowadays as the standard recipe for dental plastic direct filling materials. Methacryl derivatives of diformylated bis-(hydroxymethyl) tricyclo[5.2.1.0$^{2,6}$]-decane have also proved suitable as monomers for dental composites [W. Gruber et al., DE-A-27 14 538; W. Schmitt et al., DE-C-28 16 823; J. Reiners et al., EP-A-0 261 520]. A great disadvantage of the known polymerizable dental compositions is the polymerization shrinkage which, for example when they are used as filling material, can cause secondary caries due to the formation of edge gaps. Furthermore, in acrylate-based dental compositions, the polymerization inhibition by oxygen leads to the formation of a so-called greasy layer which, for example in the case of fillings, is undesirable and even harmful. Finally, acrylate-based polymerizable dental compositions have a low adhesion to the tooth substance.

Although there is extensive experience with epoxides and cycloaliphatic epoxides U.S. Pat. No. 2,716,123, U.S. Pat. No. 2,750,395, U.S. Pat. No. 2,863,881, U.S. Pat. No. 3,187,018), such monomers and cationically polymerizable compositions formulated therefrom having the properties necessary for dental uses have not been commercially available at any point in time.

The preparation of bifunctional cycloaliphatic epoxides is already described in patents from the 1950s (U.S. Pat. No. 2,750,395, U.S. Pat. No. 900,506, U.S. Pat. No. 907,149, U.S. Pat. No. 2,745,847, U.S. Pat. No. 2,853,499, U.S. Pat. No. 3,187,018, U.S. Pat. No. 2,863,881, U.S. Pat. No. 2,853,498). Silicon-containing cycloaliphatic epoxides have been described by Crivello et al. in various publications (EP-A-0 449 027; J. Polym. Sci., Part A: Polym. Chem., 28 (1990) 479, ibid. 31 (1993) 2563; ibid. 31 (1993) 2729; ibid. 31 (1993) 3109; ibid. 31 (1993) 3121; ibid. 33 (1995) 2463). The known cycloaliphatic epoxides are essentially low molecular weight monomers which indeed have a somewhat reduced polymerization shrinkage [J. Adhes. Sci. Technol. 9 (10) 1995, 1343; DE-A-4 340 949], but because of their high density of functional groups, do not meet the requirements (processing, physical properties) for dental uses.

Only little is known of cationically curable epoxide compositions for dental uses: The patent U.S. Pat. No. 5,556,896 describes epoxide-containing compositions which must necessarily comprise spiroorthocarbonates as shrinkage-compensating monomers. The company Ciba described in 1958, in the patent AT-A-204 687, epoxide dental compositions based on bisphenol A which were cured by means of Lewis acid catalysts. The long curing time and the low mechanical strength and long-term stability were problematic in these formulations. The companies Minnesota Mining and Manufacturing Company and Wictorin et al. describe in patents (WO 96/13538 and WO 95/30402) cationically curable epoxy mixtures, preferably with 3,4-epoxycyclohexyl-methyl 3,4-epoxycyclohexanecarboxylate or bis(3,4-epoxycyclohexyl adipate). This type of epoxide is highly cytotoxic and in vitro tests showed for these monomers mutagenic properties, which are undesirable in dental use.

The object of the present invention is to provide polymerizable compositions which, by comparison with the known compositions, in addition to a high reactivity and the necessary mechanical properties, have a low volume shrinkage and have no mutagenic and only mild cytotoxic properties.

According to the invention, this object is achieved by polymerizable compositions comprising (a) 3 to 80 wt. %, preferably 3 to 75 wt. %, and in particular 5 to 70 wt. % of an epoxide or a mixture of epoxides of the general formula:

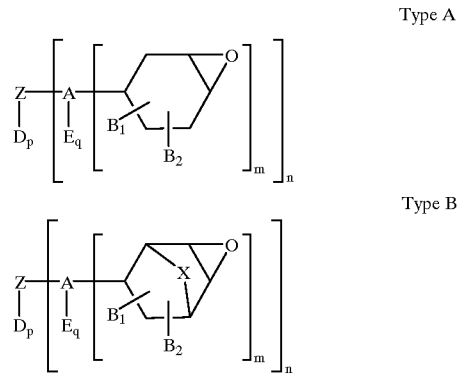

Type A

Type B in which, for type A:

if n=2

Z denotes a cycloaliphatic or aromatic radical having 1 to 22, preferably 1 to 18 C atoms or a combination of these radicals, wherein one or more C atoms can be replaced by O, C=O, —O(C=O)—, SiR$_2$ and/or NR, or an aliphatic radical having 0 to 22, preferably 1 to 18 C atoms, wherein one or more C atoms can be replaced by O, C=O, —O(C=O)—, NR or SiR$_2$, wherein at least one C atom must be replaced by SiR$_2$, and wherein R is an aliphatic radical having 1 to 7 C atoms, wherein one or more C atoms can be replaced by O, C=O and/or —O(C=O)—.

if n>2

Z denotes an aliphatic, cycloaliphatic or aromatic radical having 0 to 22, preferably 0 to 18 C atoms or a combination of these radicals, wherein one or more C atoms can be replaced by O, C=O, —O(C=O)—, SiR$_2$ and/or NR and wherein R is an aliphatic radical having 1 to 7 C atoms, wherein one or more C atoms can be replaced by O, C=O and/or —O(C=O)—, and in which, for type B:

Z denotes an aliphatic, cycloaliphatic or aromatic radical having 0 to 22, preferably 0 to 18 C atoms or a combination of these radicals, wherein one or more C atoms can be replaced by O, C=O, —O(C=O)—, SiR$_2$ and/or NR and wherein R is an aliphatic radical having 1 to 7 C atoms, wherein one or more C atoms can be replaced by O, C=O and/or —O(C=O)—, and in which, for type A and type B:

A denotes an aliphatic, cycloaliphatic or aromatic radical having 1 to 18, preferably 1 to 15 C atoms or a combination of these radicals, wherein one or more C atoms can be replaced by O, C=O, —O(C=O)—, SiR$_2$ and/or NR, wherein R is an aliphatic radical having 1 to 7 C atoms, in which one or more C atoms can be replaced by O, C=O and/or —O(C=O)—, B$_1$, B$_2$, D and E independently of one another denote an H atom or an aliphatic radical having 1 to 9, preferably 1 to 7 C atoms, wherein one or more C atoms can be replaced by O, C=O, —O(C=O)—, SiR$_2$ and/or NR, wherein R is an aliphatic radical having 1 to 7 C atoms, in which one or more C atoms can be replaced by O, C=O and/or —O(C=O)—, n denotes 2–7, preferably 2–5, in particular 2–4,
m denotes 1–10, preferably 1–7, in particular 1–5,
p denotes 1–5, preferably 1–4, in particular 1 or 2,
q denotes 1–5, preferably 1–4, in particular 1 or 2, and
x denotes CH$_2$, S or O, (b) 0 to 80, preferably 0 to 70 wt. % of an epoxide or a mixture of epoxides which differ from (a), (c) 3 to 85, preferably 5 to 75 wt. % of fillers, (d) 0.01 to 25, preferably 0.01 to 20 wt. % of initiators, retardants and/or accelerators, (e) 0 to 25, preferably 0 to 20 wt. % of auxiliaries, the percentage data in each case being based on the total weight of the composition.

Preferred compositions according to the invention comprise, as component (a), one or more of the epoxides listed below:

i) 2,2-bis[4,1-phenylenoxy-3,1-propanediyl-3,4-epoxy-cyclohexylcarboxylic acid ester]propylidene

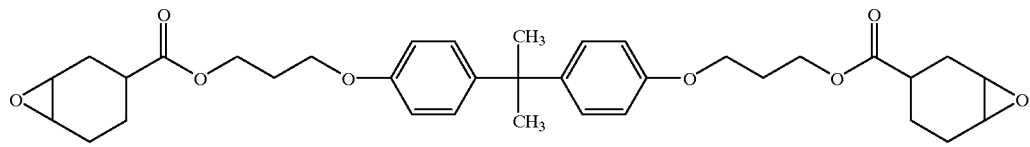

ii) 2,2-bis[4,1-phenylenoxy-3,1-propanediyl-oxy-methanediyl-3,4-epoxycyclohexyl]propylidene

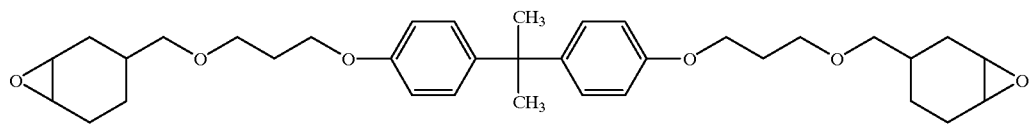

iii) 2,2-bis[3,4-epoxycyclohexylmethanediyl(4,1-phenylenoxy-3,1-propylcarboxylic acid ester)]propylidene

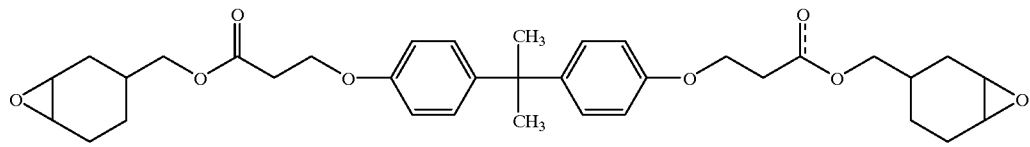

iv) 2,2-bis[4,1-phenylenoxy-3,1-propanediyl-1,1,3,3-tetramethyldisiloxanyl-1,2-ethanediyl-3,4-epoxycyclohexyl]propylidene

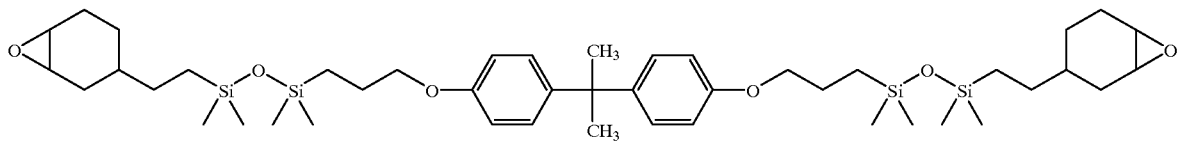

v) 2,2-bis{4,1-phenylenoxy-3,1-propanediyl-3-oxatricyclo[3.2.1.0²,⁴]octyl-6-carboxy}propylidene

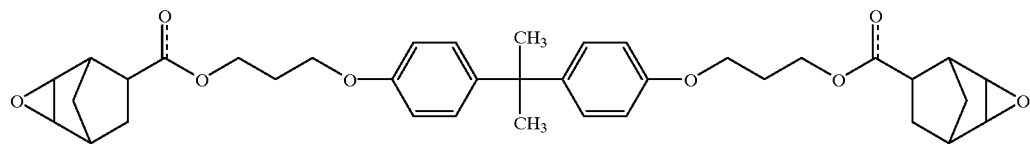

vi) 2,2-bis{4,1-phenylenoxy-3,1-propanediyl-3,8-dioxatricyclo[3.2.1.0²,⁴]octyl-6-carboxy}propylidene

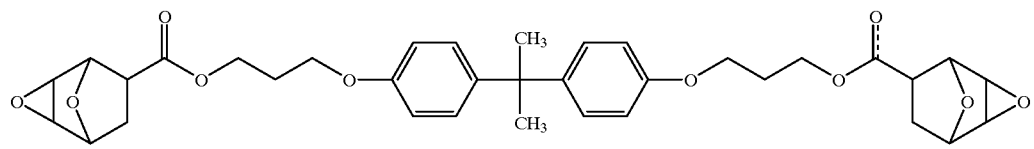

vii) 2,2-bis{4,1-phenylenoxy-3,1-propanediyl-[3,5,7-tris(ethanediyl-3,4-epoxycyclohexyl)-1,3,5,7-tetramethylcyclotetrasiloxanyl]}propylidene

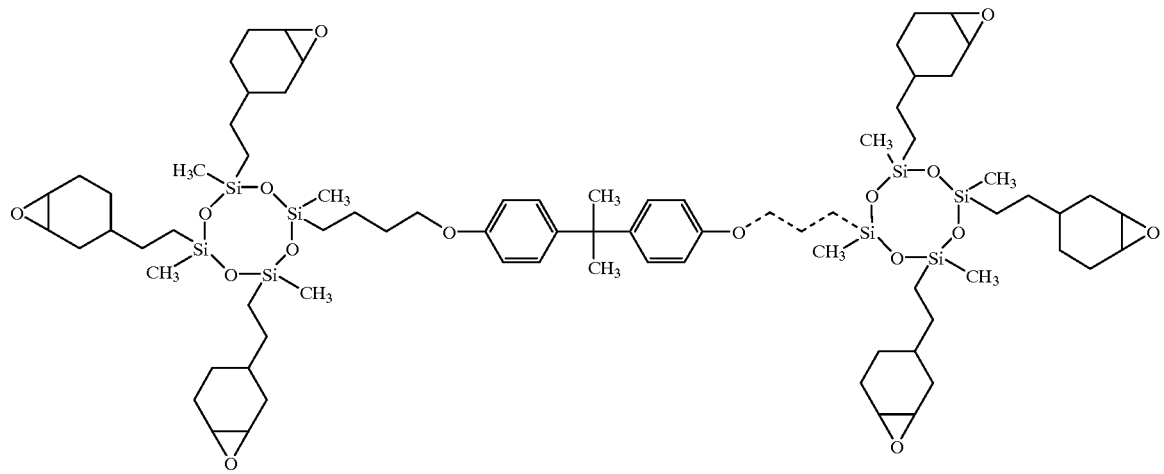

viii) bis[methanediyl-oxy-3,1-propanediyl-3,4-epoxycyclohexylcarboxylic acid ester]tricyclo[5.2.1.0²,⁶]decane

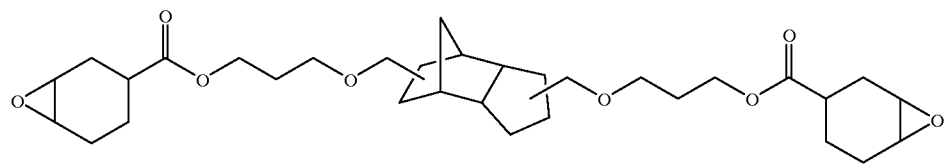

ix) bis[methanediyl-oxy-3,1-propanediyl-oxy-methanediyl-3,4-epoxycyclohexyl]tricyclo[5.2.1.0$^{2,6}$]decane

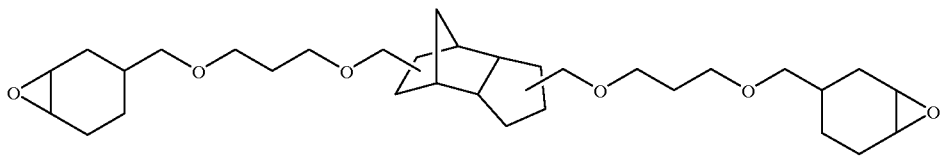

x) bis[3,4-epoxycyclohexylmethanediyl-propanecarboxylic acid-1-oxy-methanediyl]tricyclo[5.2.1.0$^{2,6}$]decane

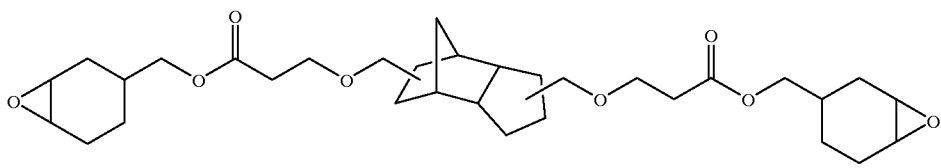

xi) bis(methanediyl-oxy-3,1-propanediyl-1,1,3,3-tetramethyldisiloxanediyl-1,2-ethanediyl-3,4-epoxycyclohexyl)tricyclo[5.2.1.0$^{2,6}$]decane

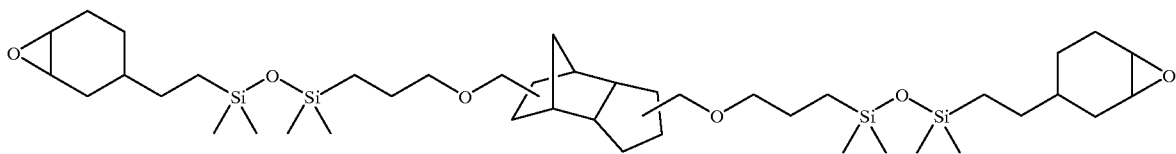

xii) bis{methanediyl-oxy-3,1-propanediyl-3-oxatricyclo[3.2.1.0$^{2,6}$]octyl-6-carboxyl}tricyclo[5.2.1.0$^{2,6}$]decane

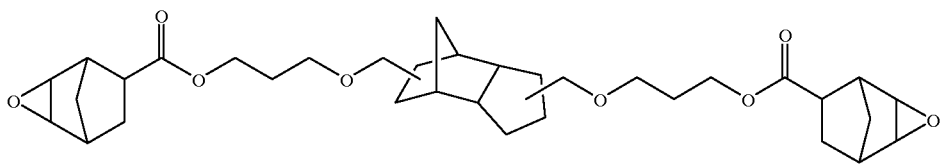

xiii) bis{methanediyl-oxy-3,1-propanediyl-3,8-dioxatricyclo[3.2.1.0$^{2,6}$]octyl-6-carboxyl}tricyclo[5.2.1.0$^{2,6}$]decane

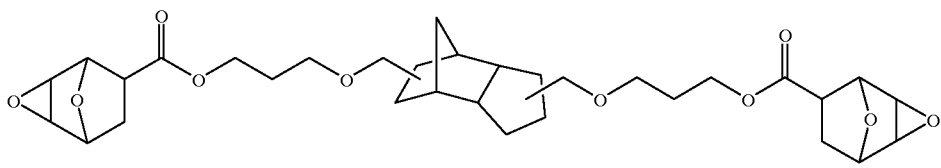

xiv) bis(methanediyl-oxy-(3-propanediyl-3,5,7-tris(2,1-ethanediyl-3,4-epoxycyclohexyl)-1,3,5,7-tetramethylcyclotetrasiloxanyl)-tricyclo[5.2.1.0$^{2,6}$]decane

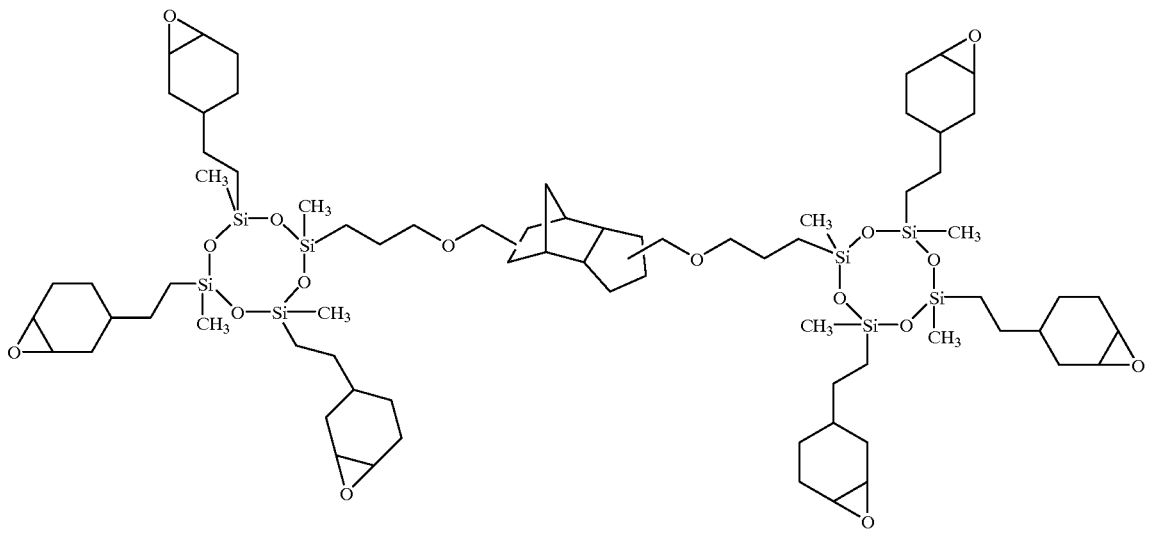

xv) 1,1,1-tris[methanediyl-oxy-methanediyl-3,4-epoxycyclohexyl]propane

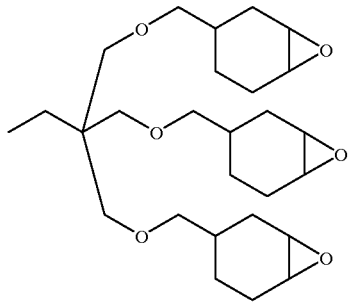

xvi) 1,1,1-tris[methanediyl-oxy-1,3-propanediyl-1,1,3,3-tetramethyldisiloxanediyl-1,2-ethanediyl-3,4-epoxycyclohexyl]propane

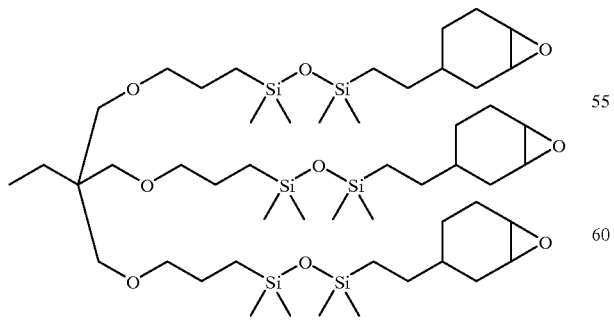

xvii) 1,1,1-tris{methanediyl-3-oxatricyclo[3.2.1.0$^{2,4}$]octyl-6-carboxy}propane xviii) 1,1,1-tris{methanediyl-3,8-dioxatricyclo[3.2.1.0$^{2,4}$]octyl-6-carboxy}propane

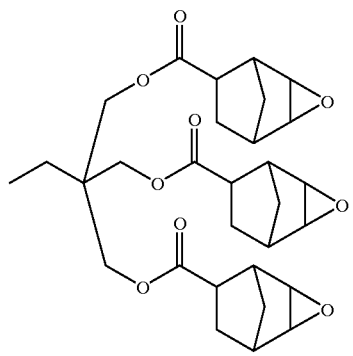

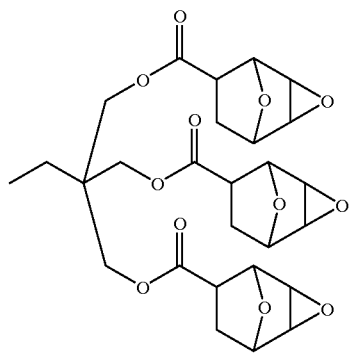

xix) 1,1,1-tris[methanediyl-oxy-3,1-propanediyl-3,5,7-tris(2,1-ethanediyl-3,4-epoxycyclohexyl)-1,3,5,7-tetramethylcyclotetrasiloxanyl]propane

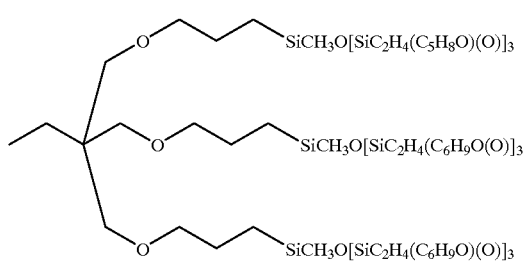

xx) 1,1,1-tris[methanediyl-oxy-bis(ethanediyloxy)-3,4-epoxycyclohexylcarboxylic acid ester]propane

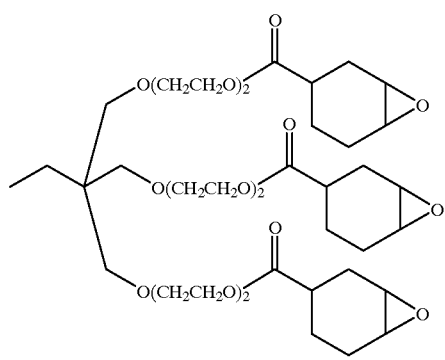

xxi) 1,1,1-tris[methanediyl-oxy-bis(ethanediyloxy)-methanediyl-3,4-epoxycyclohexyl]propane

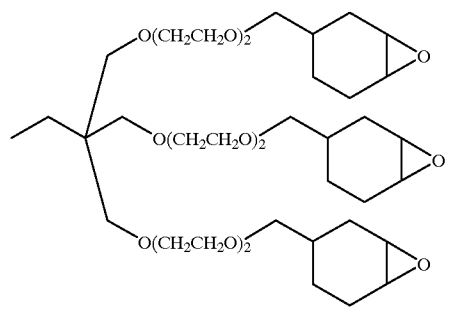

xxii) 1,1,1-tris[methanediyl-oxy-bis(ethanediyloxy)-propanediyl-1,1,3,3-tetramethyldisiloxanyl-1,2-ethanediyl-3,4-epoxycyclohexyl]propane

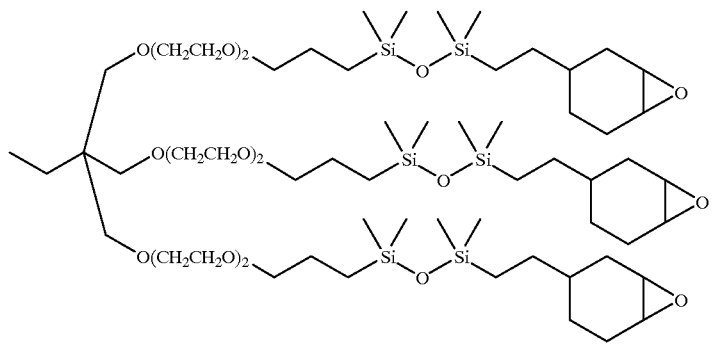

xxiii) 1,1,1-tris{methanediyl-oxy-bis(ethanediyloxy)-3-oxatricyclo[3.2.1.0$^{2,4}$]octyl-6-carboxy}propane

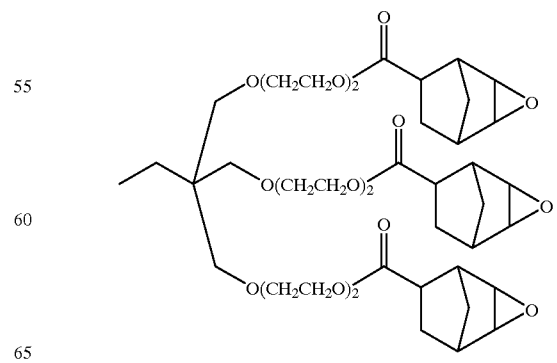

xxiv) 1,1,1-tris{methanediyl-oxy-bis(ethanediyloxy)-3,8-dioxatricyclo[3.2.1.0$^{2,4}$]octyl-6-carboxy}propane xxvii) α,ω-bis{3-oxatricyclo[3.2.1.0$^{2,4}$]octyl-6-carboxy}polytetrahydrofuran

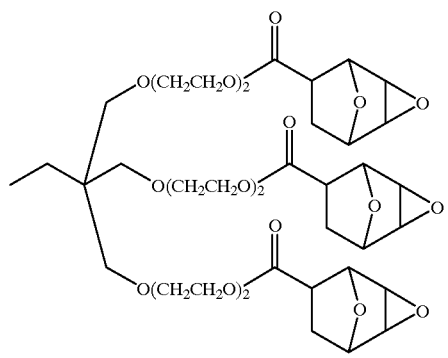

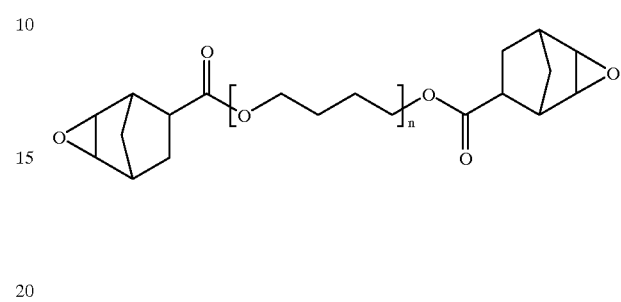

xxviii) α,ω-bis{3,8-dioxatricyclo[3.2.1.0.$^{2,4}$]octyl-6-carboxy}polytetrahydrofuran xxv) 1,1,1-tris[methanediyl-oxy-bis(ethanediyloxy)-propanediyl-3,5,7-tris(2,1-ethanediyl-3,4-epoxycyclohexyl)-1,3,5,7-tetramethylcyclotetrasiloxanyl]propane

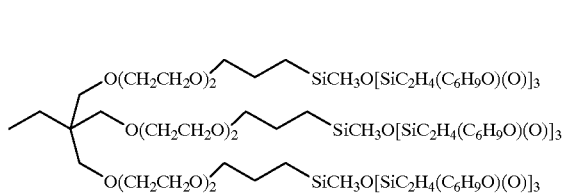

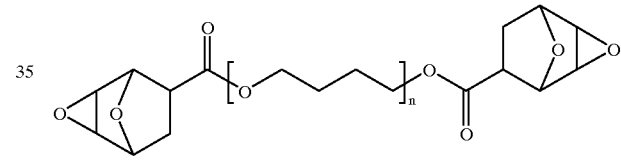

xxvi) α,ω-bis[3,4-epoxycyclohexylethanediyl-1,1,3,3-tetramethyldisiloxanyl-3,1-propanediyl]polytetrahydrofuran xxix) α,ω-bis(3-propanediyl-3,5,7-tris(2,1-ethanediyl-3,4-epoxycyclohexyl)-1,3,5,7-tetramethylcyclotetrasiloxanyl)polytetrahydrofuran

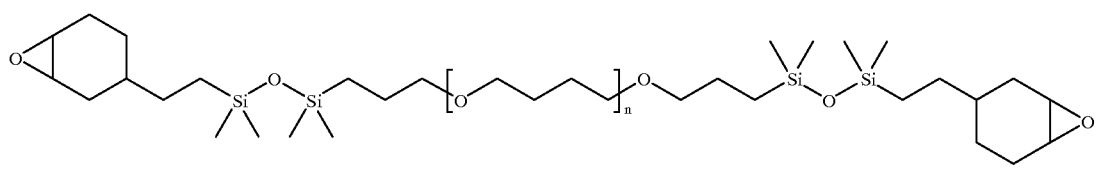

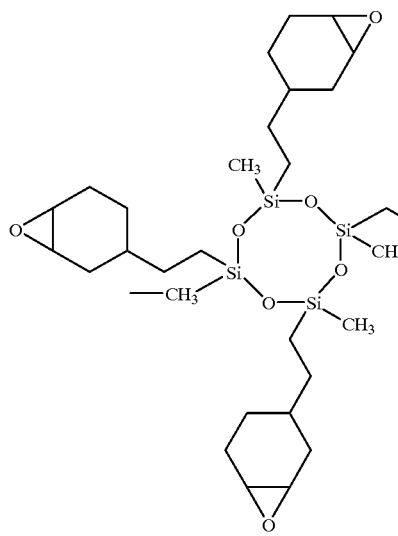
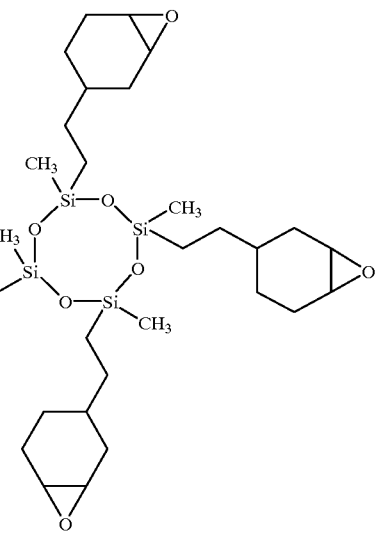

The invention also relates to the abovementioned, individually listed new cycloaliphatic epoxides per se.

The epoxides can be prepared in a simple manner. To prepare the epoxides of type A without siloxanyl units, the cycloaliphatic alkenes obtained by conventional etherification or esterification of di-, tri- or polyols with cyclohexenecarboxylic acid or cyclohexenylmethanol are epoxidized with perbenzoic acid in suitable solvents, preferably in diethyl ether. When the reaction has ended, the mixture is washed several times with sodium hydroxide solution and dried over magnesium sulphate. The volatile constituents are distilled off in vacuo.

The epoxides of type A with siloxanyl units are prepared by two-stage conventional hydrosilylations: Compounds having two, three or more terminal alkene functions are added to an excess of a siloxane having at least two active hydrogen atoms and catalytic amounts of $H_2PtCl_6$, dissolved in a suitable solvent (e.g. hexane). When the reaction has ended, the mixture is freed from the platinum which has precipitated out, washed once with water and dried over magnesium sulphate. In a second hydrosilylation, the resulting di-, tri- or polysiloxane-containing compound is dissolved in a suitable solvent, e.g. in toluene or alkanes, and heated with $H_2PtCl_6$ and vinylcyclohexene epoxide. The mixture is freed from the platinum which has precipitated out and washed once with water. The product is obtained by distilling off the volatile constituents in vacuo.

To prepare epoxides of type B with terminal 3-oxatricyclo [3.2.1.0$^{2,4}$]octanyl units, di- tri- or poly(meth)acrylates are reacted with substituted (or unsubstituted) monomeric cyclopentadiene, thiophenes or furans under Lewis acid catalysis (for example $ZnCl_2$ or $AlCl_3$) under normal pressure or in an autoclave to give the corresponding Diels-Alder products. The endocyclic double bond is epoxidized with perbenzoic acid in a suitable solvent, preferably in diethyl ether. When the reaction has ended, the mixture is washed several times with sodium hydroxide solution and dried over magnesium sulphate. The volatile constituents are distilled off in vacuo.

In addition to the epoxides according to the invention, the polymerizable compositions according to the invention can comprise, as component (b), other low-viscosity epoxides. Low-viscosity epoxides according to (b) can be, for example: 3,4-epoxycyclohexylmethyl 3,4-epoxycyclohexanecarboxylate (U.S. Pat. No. 2,716,123), 3,4-epoxy-6-methylcyclohexyl 3,4-epoxy-6-methylcyclohexanecarboxylate (U.S. Pat. No. 2,716,123) or related epoxides, vinylcyclohexene diepoxide (U.S. Pat. No. 2,948,688), dicyclopentadiene dioxide (U.S. Pat. No. 2,985,667), bis(3,4-epoxycyclohexylmethyl) adipate (U.S. Pat. No. 2,750,395, U.S. Pat. No. 2,863,881, U.S. Pat. No. 3,187,018), 1,3,5,7-tetrakis(2,1-ethanediyl-3,4-epoxycyclohexyl)-1,3,5,7-tetramethylcyclotetrasiloxane of the following formula:

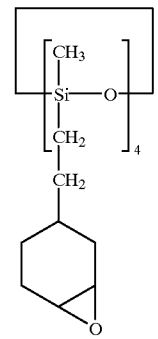

1,3,5,7,9-pentakis(2,1-ethanediyl-3,4-epoxycyclohexyl)-1,3,5,7,9-pentamethylcyclopentasiloxane (U.S. Pat. No. 5,085,124) of the following formula:

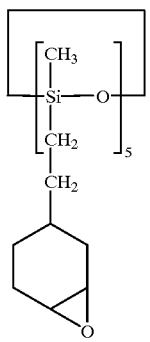

and low molecular weight siloxanes functionalized with cycloaliphatic epoxides, for example 1,1,3,3-tetramethyl-1,3-bis(ethanediyl-3,4-epoxycyclohexyl)disiloxane (EP-A-0 449 027, EP-A-0 574 265) of the following formula:

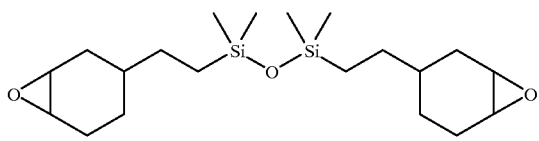

The low-viscosity epoxides according to component (b) are present in a concentration of 0 to 80 wt. %, preferably 5 to 75 wt. %, in each case based on the total weight of the composition.

Inorganic fillers according to component (c) can be the customary dental fillers, for example quartz, ground, optionally X-ray-opaque, optionally reactive glasses, sparingly soluble fluorides, such as $CaF_2$ or $YF_3$ (EP-B-0 238 025), silica gels and pyrogenic silicic acid or granules thereof. The compositions can also comprise, as fluoride-donating constituents, one or more water-soluble inorganic complex fluorides of the general formula $A_nMF_m$, wherein A denotes a mono- or polyvalent cation, M denotes a metal of main group or sub-group III, IV or V, n denotes an integer from 1 to 3 and m denotes an integer from 4 to 6 (DE-A-4 445 266). The dental compositions contain these in a concentration of 3 to 85 wt. %, preferably 5 to 75 wt. %, and in particular 30 to 75 wt. %, based on the total composition. For better incorporation into the polymer matrix, it maybe advantageous to hydrophobize the fillers and, if appropriate, the X-ray-opaque additives, such as $YF_3$. Customary hydrophobizing agents are silanes, for example trimethoxyglycidylsilane. The maximum particle size of the inorganic fillers is preferably 20 μm, in particular 12 μm. Fillers having an average particle size <7 μm are especially preferably employed.

Initiators according to component (d) of the compositions according to the invention can be: Lewis or Broensted acids, or compounds which liberate such acids, which initiate the polymerization, for example $BF_3$ or ether adducts thereof ($BF_3.THF$, $BF_3.Et_2O$, etc.), $AlCl_3$, $FeCl_3$, $HPF_6$, $HAsF_6$, $HSbF_6$ or $HBF_4$, or substances which initiate the polymerization after irradiation by UV or visible light or by means of heat and/or pressure, such as e.g. (eta-6-cumene)(eta-5-cyclopentadienyl)iron hexafluorophosphate, (eta-6-cumene)(eta-5-cyclopentadienyl)iron tetrafluoroborate, (eta-6-cumene)(eta-5-cyclopentadienyl)iron hexafluoroantimonate, substituted diaryliodonium salts and triarylsulphonium salts. Accelerators which can be employed are peroxy compounds of the perester, diacyl peroxide, peroxydicarbonate and hydroperoxide type. Hydroperoxides are preferably used, and cumene hydroperoxide in an approximately 70 to 90% solution in cumene is employed as the particularly preferred accelerator. The ratio of photoinitiator to cumene hydroperoxide can be varied within wide limits from 1:0.001 to 1:10, but the ratio used is preferably 1:0.1 to 1:6, and particularly preferably 1:0.5 to 1:4. The use of complexing agents, such as, for example, oxalic acid, 8-hydroxyquinoline, ethylenediaminetetraacetic acid and aromatic polyhydroxy compounds, is also possible. Retardants which can be added are bases, typically tertiary amines. Component (d) is present in the composition according to the invention in an amount of 0.01 to 25 wt. %, preferably 0.01 to 20 wt. %, based on the total weight of the composition.

Suitable auxiliaries according to component (e) can be, for example, stabilizers, pigments or diluents usually employed in the dental field.

The epoxide-containing polymerizable compositions according to the invention are particularly suitable as materials for dental purposes, for example for the production of artificial teeth or temporary prostheses, as coating compositions, for gluing substrates and as dental filling materials.

The polymerizable compositions according to the invention offer a particular advantage in dental uses. The volume shrinkage of the compositions according to the invention is far below the shrinkage of known compositions based on methacrylate monomers. As a result, for example, the edge gap problem of filling materials can be largely avoided. The dimensional stability and the storage stability of the epoxides according to the invention and of the polymerizable compositions prepared therefrom is also of great advantage in the case of precision model materials.

Compared with acrylate-based dental compositions, which have a very short setting time and therefore a sudden curing compared with epoxide-based compositions, the compositions according to the invention show a hardening which proceeds uniformly over a period of, for example, 10 to 240 seconds. Stresses within the polymers formed are thus avoided. The compositions according to the invention therefore also have an optimum processing time, before they reach their final hardness.

In addition to high compressive and flexural strengths, the polymerizable compositions according to the invention surprisingly show high impact strengths, which is of outstanding importance for dental uses.

The dental filling materials according to the invention moreover show a surprisingly good adhesion to the tooth substance. The epoxides according to the invention furthermore are not mutagenic and are acceptable in respect of their cytotoxicity.

EXAMPLES OF THE SYNTHESIS OF THE MONOMERS ACCORDING TO THE INVENTION

1. Preparation of 2,2-Bis[4,1-phenylenoxy-3,1-propanediyl-3,4-epoxycyclohexylcarboxylic Acid Ester]propylidene 100 g 2,2-bis(4-oxypropylhydroxyphenyl)propane are kept under reflux with 85 g 4-cyclohexenecarboxylic acid in toluene for 6 hours. The solvent and excess 4-cyclohexenecarboxylic acid are distilled off. 161 g 2,2-bis(4-oxypropylphenyl-3-cyclohexenylcarboxylate)propane remain and are added to 83 g perbenzoic acid in 500 ml diethyl ether. After a reaction time of 8 hours, the mixture is washed several times with 10% sodium hydroxide solution and dried over magnesium sulphate. The volatile constituents are distilled off in vacuo.

2. Preparation of bis(3,4-epoxycyclohexylethyl-tetramethyldisiloxanylpropoxymethyl)-tricyclo [5.2.1.0$^{2,6}$]decane 174 g tetramethyldisiloxane are initially introduced into 800 ml hexane, and 120 mg H$_2$PtCl$_6$ are added. 80 g tricyclo[5.2.1.0$^{2,6}$] decane-diallyl ether are added and the mixture is heated at 85° C. (b.p.) for 3 hours. The mixture is freed from the platinum which has precipitated out, washed once with water and dried over magnesium sulphate. Hexane and volatile constituents are distilled off in vacuo. The resulting bis(tetramethyldisiloxanylpropoxymethyl)-tricyclo[5.2.1.0$^{2,6}$]decane is dissolved in 200 ml hexane, 120 mg H$_2$PtCl$_6$ and 71 g vinyl-3,4-cyclohexene epoxide are added and the mixture is heated at 85° C. for 3 hours. The mixture is freed from the platinum which has precipitated out, washed once with water and dried over magnesium sulphate. After the reaction mixture has been concentrated in vacuo, 202 g bis(3,4-epoxycyclohexylethyl-tetramethyldisiloxanyl-propoxymethyl)-tricyclo[5.2.1.0$^{2,6}$] decane are obtained.

3. Preparation of α,ω-bis(3-propanediyl-3,5,7-tris(2, 1-ethanediyl-3,4-epoxycyclohexyl)-1,3,5,7-tetramethylcyclotetrasiloxanyl)-polytetrahydrofuran 126 g α,ω-polytetrahydrofuran-600-diallyl ether are added to 151 g 1,3,5,7-tetramethylcyclotetrasiloxane and 110 mg H$_2$PtCl$_6$ in 700 ml hexane. After 3 hours at 85° C., the platinum which has precipitated out is separated off and all the volatile constituents are distilled off in vacuo. α,ω-Bis[3,5,7-tris(3,4-epoxycyclohexylethyl)-3-propyl-1,3,5,7-tetramethylcyclotetrasiloxanyl]-polytetrahydrofuran remains and is heated at 120° C. with 179 g vinylcyclohexene epoxide and 130 mg H$_2$PtCl$_6$ in 800 ml toluene for 3 hours. The platinum which has precipitated out is separated off and all the volatile constituents are distilled off in vacuo. 339 g α,ω-bis[3,5,7-tris(3,4-epoxycyclohexylethyl)-3-propyl-1,3,5,7-tetramethylcyclotetrasiloxanyl]-polytetrahydrofuran remain.

4. Preparation of α,ω-bis(6-methyl-dioxatricyclo [3.2.1.0$^{2,4}$]octyl-6-carboxy)polyethylene Glycol 85 g α,ω-polyethylene glycol-600-dimethacrylate are heated at 120° C. with 19 g furan in 300 ml toluene in an autoclave under 10 bar for 4 hours. The volatile constituents are distilled off in vacuo. α,ω-Bis(3-methyl-7-oxabicyclo [2.2.1]heptyl-3-carboxy)polyethylene glycol remains and is added dropwise to a solution of 31 g perbenzoic acid in 300 ml diethyl ether. After a reaction time of 8 hours, the mixture is washed several times with 10% sodium hydroxide solution and dried over magnesium sulphate. The volatile constituents are distilled off in vacuo.

5. Preparation of 1,1,1-tris[methanediyl-oxy-bis (ethanediyl-oxy)-methanediyl-3,4-epoxycyclohexyl] propane 168 g 1,1,1-tris(methanediyl-hydroxy-bis (ethanediyloxy)]propane are initially introduced into 600 ml tetrahydrofuran. 178 g potassium tert-butanolate are added in portions and the mixture is stirred at 30° C. for one hour. 277 g 3-cyclohexenylbromomethane, dissolved in 300 ml tetrahydrofuran, are then added dropwise. The reaction mixture is heated at 75° C. for 24 hours. The solvent is distilled off, the mixture is suspended in methyl tert-butyl ether and the precipitate is filtered off. After aqueous extraction, 249 g 1,1,1-tris[methanediyl-oxy-bis (ethanediyloxy)-methanediyl-3-cyclohexenyl]propane remain and are dissolved in 500 ml diethyl ether. This solution is added to 61 g perbenzoic acid in 400 ml diethyl ether and, after a reaction time of 8 hours, the mixture is washed several times with 10% sodium hydroxide solution. The mixture is dried over magnesium sulphate and the volatile constituents are distilled off in vacuo.

Examples of Polymerizable Compositions
1. General Preparation of Polymerizable Compositions
  1.1 One-component photo- or UV-curing systems
  The preparation of the one-component compositions which can be polymerized according to the invention is a two-stage process in which homogeneous premixing of all the constituents with the exception of the photoinitiator takes place in the first stage. In a second stage, the photoinitiator is kneaded homogeneously into the paste with exclusion of light. When the epoxy resins according to the invention which have been obtained in this way and can be processed have been mixed in completely, they are introduced into light-proof containers.
  1.2 Two-component systems
  The two-component compositions which can be polymerized according to the invention are prepared by first preparing a homogeneously mixed component A comprising the epoxide monomers, a filler content, the retardants, accelerators and the auxiliaries. A homogeneously mixed component B comprising the initiator, diluent and a further filler content is furthermore prepared. Components A and B are introduced, for example, into a double-cartridge system. The two-component composition can be processed directly by a static mixer on the cartridge system.
2. Use Examples Example 1

Component A: A paste is kneaded from 17.6 parts by wt. α,ω-bis(3-propanediyl-3,5,7-tris(2,1-ethanediyl-3,4-epoxycyclohexyl)-1,3,5,7-tetramethylcyclotetrasiloxanyl)-ditetrahydrofuran, 17.6 parts by wt. 3,4-epoxycyclohexylmethyl 3,4-epoxycyclohexanecarboxylate and 64.7 parts by wt. of a silanized, pigmented quartz. A second component B comprises 32.8 parts by wt. polyethylene glycol, 4.7 parts by wt. BF$_3$.OEt$_2$ and 62.5 parts by wt. of a silanized pigmented quartz. Pastes A and B are mixed in a ratio of 2:1 via a static mixer. The composition cures within two minutes.

Example 2

A paste is kneaded from 18 parts by wt. bis(methanediyl-oxy-3,1-propanediyl-3,4-epoxycyclohexylcarboxylic acid ester)-tricyclo[5.2.1.0$^{2,6}$]decane, 10 parts by wt. 1,1,3,3-tetramethyl-1,3-bis(ethanediyl-3,4-epoxycyclohexyl) disiloxane, 68.9 parts by wt. of a silanized pigmented quartz, 1.2 parts by wt. (eta-6-cumene)(eta-5-cyclopentadienyl)iron hexafluorophosphate and 1.8 parts by wt. cumene hydroperoxide and is cured by irradiation with a lamp (Elipar II light apparatus, ESPE Dental-Medizin GmbH & Co. KG, Germany) in the course of approx. 40 seconds.

Example 3

16.7 parts by wt. 1,1,1-tris[methanediyl-oxy-1,3-propanediyl-1,1,3,3-tetramethyldisiloxanediyl-1,2- ethanediyl-3,4-epoxycyclohexyl]propane, 4.5 parts by wt. 3,4-epoxycylcohexylmethyl 3,4-epoxycyclohexanecarboxylate, 5.2 parts by wt. 1,3,5,7-tetrakis(2,1-ethanediyl-3,4-epoxycyclohexyl)-1,3,5,7-tetramethyl-cyclotetrasiloxane, 70.5 parts by wt. of a silanized pigmented quartz, 1.2 parts by wt. (eta-6-cumene)(eta-5-cyclopentadienyl)iron hexafluorophosphate and 1.9 parts by wt. cumene hydroperoxide are kneaded to a paste, which is cured by irradiation with a lamp (Elipar II light apparatus, ESPE Dental-Medizin GmbH & Co. KG, Germany) in the course of approx. 40 seconds.

Example 4

18 parts by wt. 2,2-bis[4,1-phenylenoxy-3,1-propanediyl-3,4-epoxycyclohexylcarboxylic acid ester]propylidene, 13 parts by wt. 3,4-epoxycyclohexylmethyl 3,4-epoxycyclohexanecarboxylate, 65.4 parts by wt. of a silanized pigmented quartz, 1.5 parts by wt. (eta-6-cumene)(eta-5-cyclopentadienyl)iron hexafluorophosphate and 2.1 parts by wt. cumene hydroperoxide are kneaded to a paste, which is cured by irradiation with a lamp (Elipar II light apparatus, ESPE Dental-Medizin GmbH & Co. KG, Germany) in the course of approx. 40 seconds.

Example 5

Comparison paste, commercially obtainable dental composition

|  | Example 1 | Example 2 | Example 3 | Example 4 | Example 5 (comparison) |
|---|---|---|---|---|---|
| Compressive strength [MPa] | 388 | 331 | 361 | 355 | 385 |
| Flexural strength [MPa] (ISO 4049) | 151 | 131 | 121 | 141 | 118 |
| Volume shrinkage [%] | 1.3 | 0.8 | 0.7 | 1.0 | 2.2 |

What is claimed is:

1. Polymerizable dental composition comprising
   (a) 3 to 80 wt. % of an epoxide or a mixture of epoxides of the general formula:

Type A

Type B in which, for type A:
   if n=2
   Z denotes a cycloaliphatic or aromatic radical having 1 to 22 carbon atoms or a combination of these radicals, wherein one or more carbon atoms can be replaced by O, C=O, —O(C=O)—, $SiR_2$ and/or NR, or an aliphatic radical having 0 to 22 carbon atoms, wherein one or more carbon atoms can be replaced by O, C=O, —O(C=O)—, NR or $SiR_2$, wherein at least one carbon atom must be replaced by $SiR_2$, and wherein R is an aliphatic radical having 1 to 7 carbon atoms, wherein one or more carbon atoms can be replaced by O, C=O and/or —O(O=O)—,
   if n>2
   Z denotes an aliphatic, cycloaliphatic or aromatic radical having 0 to 22 carbon atoms or a combination of these radicals, wherein one or more carbon atoms can be replaced by O, C=O, —O(C=O)—, $SiR_2$ and/or NR and wherein R is an aliphatic radical having 1 to 7 carbon atoms, wherein one or more carbon atoms can be replaced by O, C=O and/or —O(C=O)—,
   and in which, for type B:
   Z denotes an aliphatic, cycloaliphatic or aromatic radical having 0 to 22 carbon atoms or a combination of these radicals, wherein one or more carbon atoms can be replaced by O, C=O, —O(C=O)—, $SiR_2$ and/or NR and wherein R is an aliphatic radical having 1 to 7 carbon atoms, wherein one or more carbon atoms can be replaced by O, C=O and/or —O(C=O)—,
   and in which, for type A and type B:
   A denotes an aliphatic, cycloaliphatic or aromatic radical having 1 to 18 carbon atoms or a combination of these radicals, wherein one or more carbon atoms can be replaced by O, C=O, —O(C=O)—, $SiR_2$ and/or NR, wherein R is an aliphatic radical having 1 to 7 carbon atoms, in which one or more carbon atoms can be replaced by O, C=O and/or —O(C=O)—,
   $B_1$, $B_2$, D and E independently of one another denote a hydrogen atom or an aliphatic radical having 1 to 9 carbon atoms, wherein one or more carbon atoms can be replaced by O, C=O, —O(C=O)—, $SiR_2$ and/or NR, wherein R is an aliphatic radical having 1 to 7 carbon atoms, in which one or more carbon atoms can be replaced by O, C=O and/or —O(C=O)—,
   n denotes 2–7,
   m denotes 1–10,
   p denotes 1–5,
   q denotes 1–5 and
   x denotes $CH_2$, S or O,
   (b) 0 to 80 wt. % of an epoxide or a mixture of epoxides which differ from (a),
   (c) 3 to 85 wt. % of fillers,
   (d) 0.01 to 25 wt. % of initiators and retardants or accelerators,
   (e) 0 to 25 wt. % of auxiliaries, the percentage data in each case being based on the total weight of the composition wherein the initiators (d) are Lewis or Broensted acids, or compounds which liberate such acids, which initiate polymerization, or substances which initiate polymerization after irradiation by UV or visible light, or by means of heat and/or pressure, in contact with a tooth.

2. Polymerizable composition as claimed in patent claim 1, characterized in that it comprises, as component (a), one or more of the following epoxides:
   i) 2,2-bis[4,1-phenylenoxy-3,1-propanediyl-3,4-epoxycyclohexylcarboxylic acid ester]propylidene

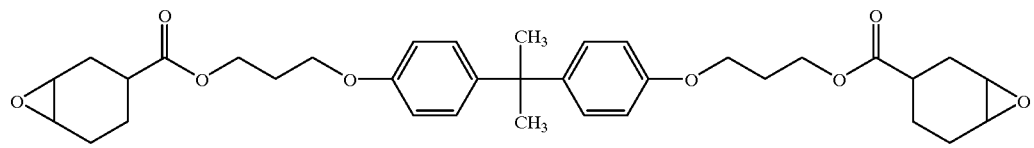

ii) 2,2-bis[4,1-phenylenoxy-3,1-propanediyl-oxy-methanediyl-3,4-epoxycyclohexyl]propylidene

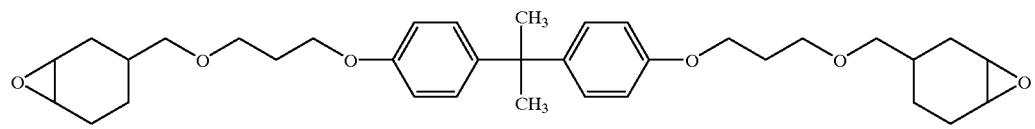

iii) 2,2-bis[3,4-epoxycyclohexylmethanediyl(4,1-phenylenoxy-3,1-propylcarboxylic acid ester)] propylidene

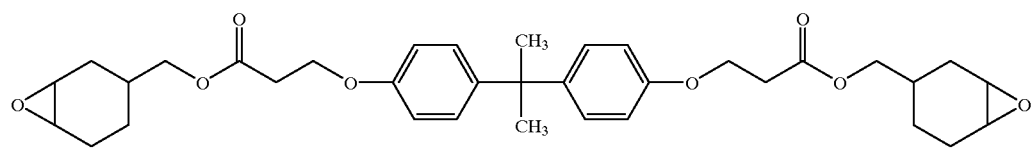

iv) 2,2-bis[4,1-phenylenoxy-3,1-propanediyl-1,1,3,3-tetramethyldisiloxanyl-1,2-ethanediyl-3,4-epoxycyclohexyl]propylidene

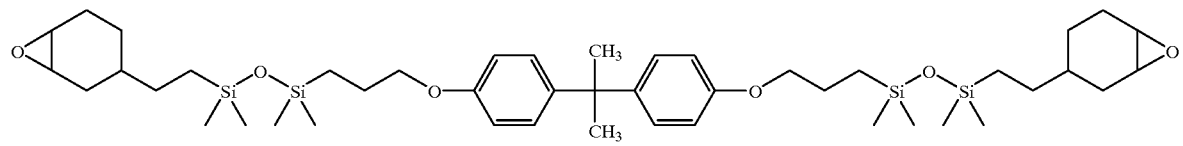

v) 2,2-bis{4,1-phenylenoxy-3,1-propanediyl-3-oxatricyclo[3.2.1.0$^{2,4}$]octyl-6-carboxy}propylidene

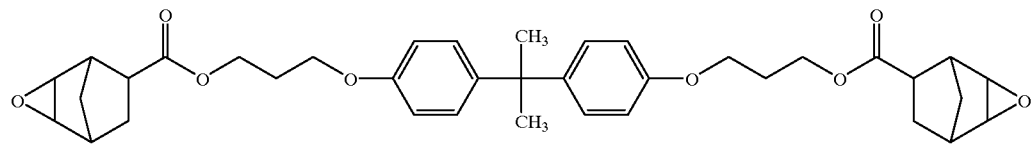

iv) 2,2-bis{4,1-phenylenoxy-3,1-propanediyl-3,8-dioxatricyclo[3.2.1.0$^{2,4}$]octyl-6-carboxy}propylidene

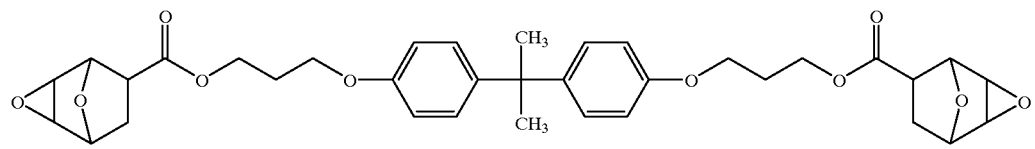

vii) 2,2-bis{4,1-phenylenoxy-3,1-propanediyl-[3,5,7-tris(ethanediyl-3,4-epoxycyclohexyl)-1,3,5,7-tetramethylcyclotetrasiloxanyl]}propylidene

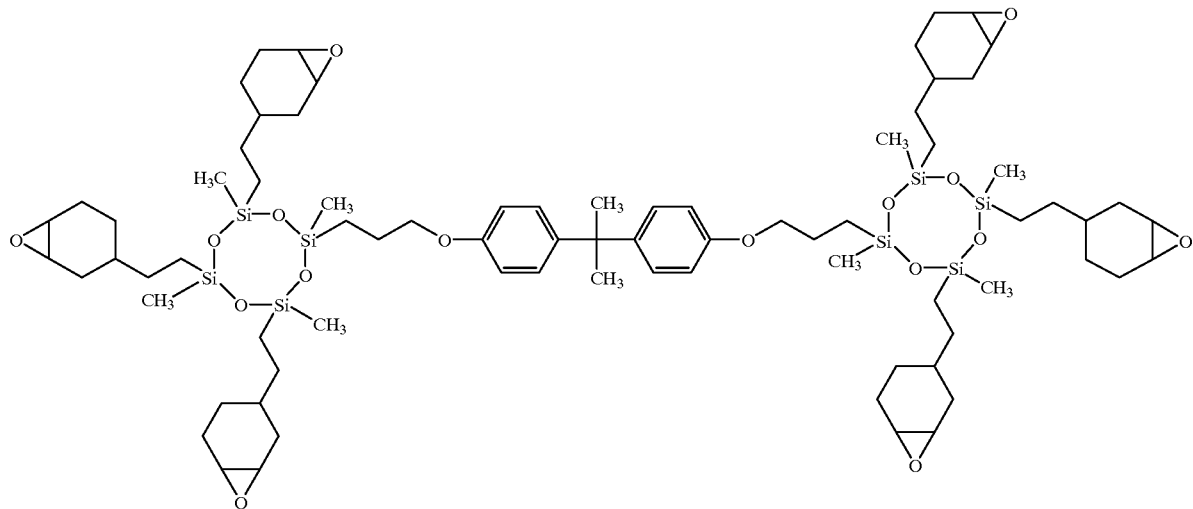

viii) bis[methanediyl-oxy-3,1-propanediyl-3,4-epoxycyclohexylcarboxylic acid ester]tricyclo[5.2.1.0$^{2,6}$]decane

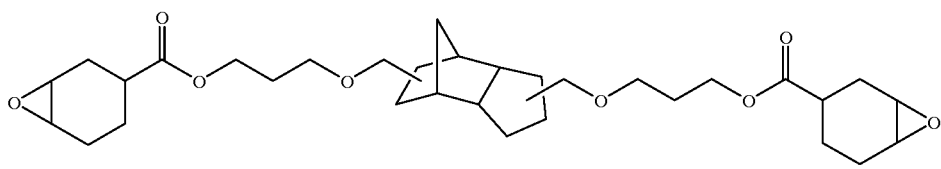

ix) bis[methanediyl-oxy-3,1-propanediyl-oxy-methanediyl-3,4-epoxycyclohexyl]tricyclo[5.2.1.0$^{2,6}$]decane

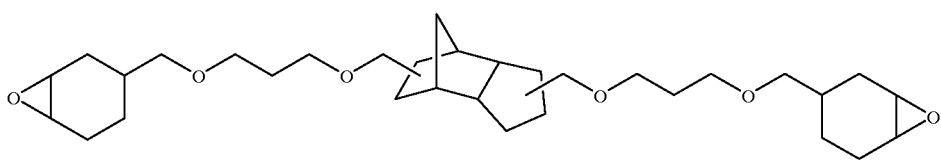

x) bis[3,4-epoxycyclohexylmethanediyl-propanecarboxylic acid-1-oxy-methanediyl]tricyclo[5.2.1.0$^{2,6}$]decane

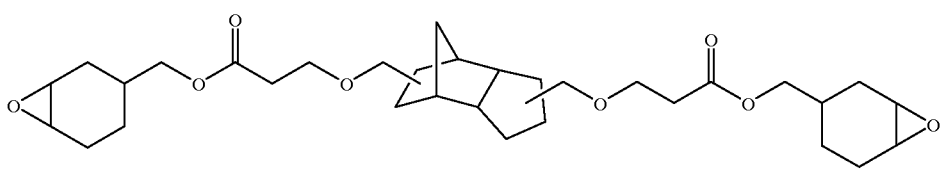

xi) bis(methanediyl-oxy-3,1-propanediyl-1,1,3,3-tetramethyldisiloxanediyl-1,2-ethanediyl-3,4-epoxycyclohexyl)tricyclo[5.2.1.0$^{2,6}$]decane

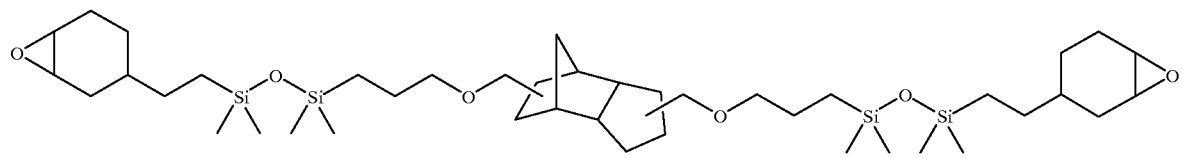

xii) bis{methanediyl-oxy-3,1-propanediyl-3-oxatricyclo[3.2.1.0$^{2,6}$]octyl-6-carboxyl}tricyclo[5.2.1.0$^{2,6}$]decane

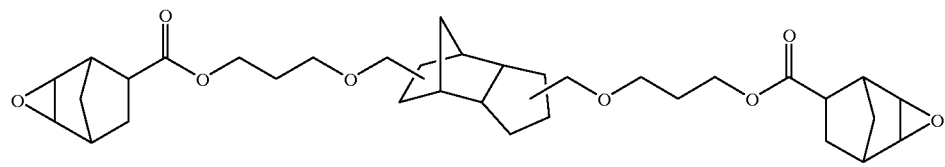

xiii) bis{methanediyl-oxy-3,1-propanediyl-3,8-dioxatricyclo[3.2.1.0$^{2,6}$]octyl-6-carboxyl}tricyclo[5.2.1.0$^{2,6}$]decane

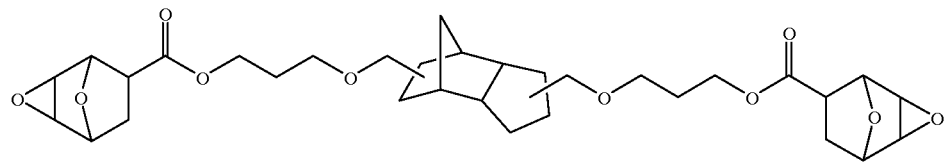

xiv) bis(methanediyl-oxy-(3-propanediyl-3,5,7-tris(2,1-ethanediyl-3,4-epoxycyclohexyl)-1,3,5,7-tetramethylcyclotetrasiloxanyl)tricyclo[5.2.1.0$^{2,6}$]decane

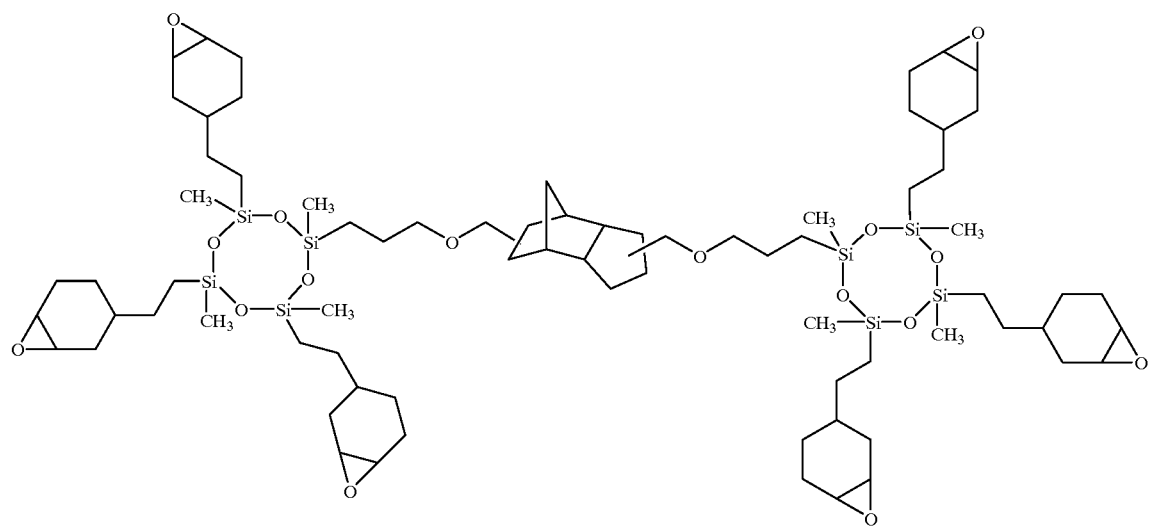

xv) 1,1,1-tris[methanediyl-oxy-methanediyl-3,4-epoxycyclohexyl]propane

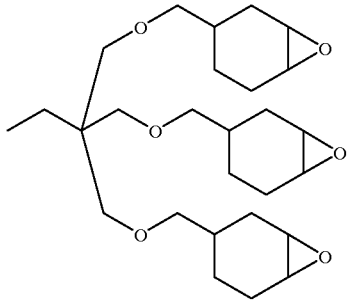

xvi) 1,1,1-tris[methanediyl-oxy-1,3-propanediyl-1,1,3,3-tetramethyldisiloxanediyl-1,2-ethanediyl-3,4-epoxycyclohexyl]propane

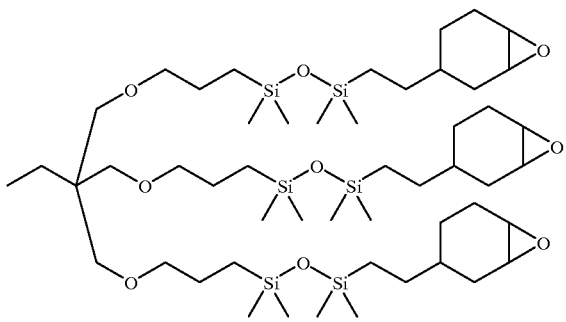

xvii) 1,1,1-tris{methanediyl-3-oxatricyclo[3.2.1.0$^{2,4}$]octyl-6-carboxy}propane

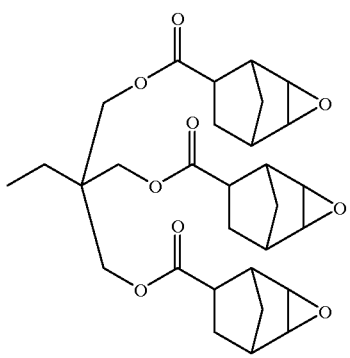

xviii) 1,1,1-trist{methanediyl-3,8-dioxatricyclo[3.2.1.0$^{2,4}$]octyl-6-carboxy}propane

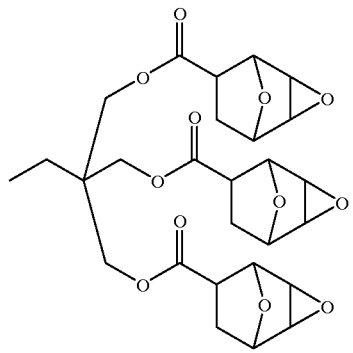

xix) 1,1,1-tris[methanediyl-oxy-3,1-propanediyl-3,5,7-tris(2,1-ethanediyl-3,4-epoxycyclohexyl)-1,3,5,7-tetramethylcyclotetrasiloxanyl]propane

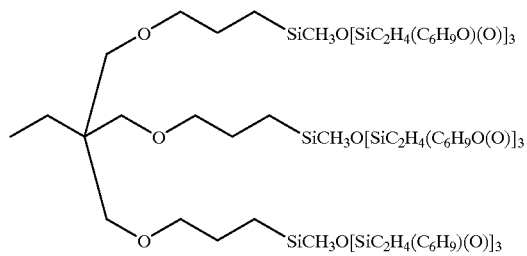

xx) 1,1,1-tris[methanediyl-oxy-bis(ethanediyloxy)-3,4-epoxycyclohexylcarboxylic acid ester]propane

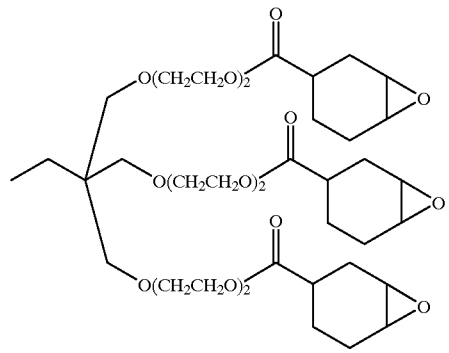

xxi) 1,1,1-tris[methanediyl-oxy-bis(ethanediyloxy)-methanediyl-3,4-epoxycyclohexyl]propane

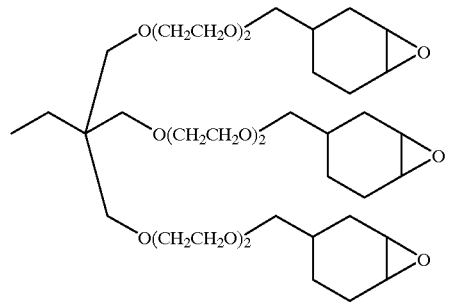

xxii) 1,1,1-tris[methanediyl-oxy-bis(ethanediyloxy)-propanediyl-1,1,3,3-tetramethyldisiloxanyl-1,2-ethanediyl-3,4-epoxycyclohexyl]propane

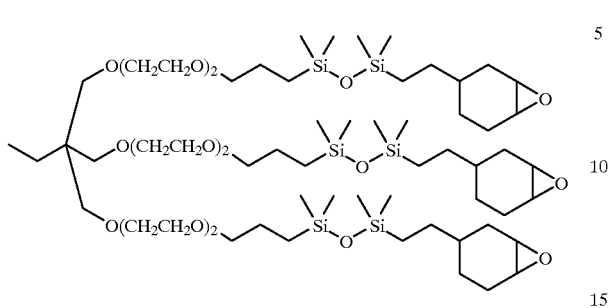

xxii) 1,1,1-tris{methanediyl-oxy-bis(ethanediyloxy)-3-oxatricyclo[3.2.1.0$^{2,4}$]octyl-6-carboxy}propane

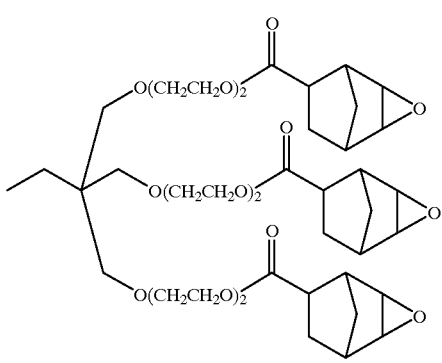

xxiv) 1,1,1-tris{methanediyl-oxy-bis(ethanediyloxy)-3,8-dioxatricyclo[3.2.1.0$^{2,4}$]octyl-6-carboxy}propane

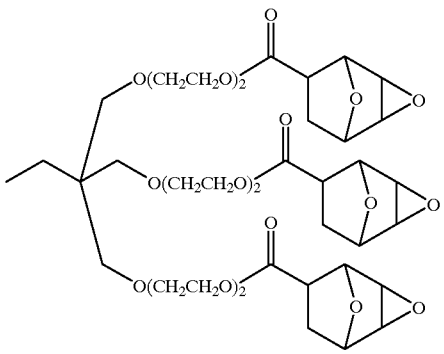

xxv) 1,1,1,1-tris[methanediyl-oxy-bis(ethanediyloxy)-propanediyl-3,5,7-tris(2,1-ethanediyl-3,4-epoxycyclohexyl)-1,3,5,7-tetramethylcyclo-letrasiloxanyl]propane

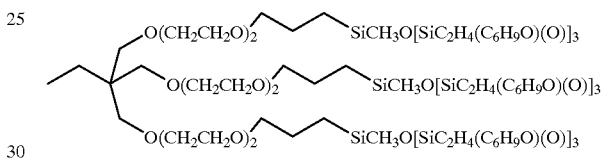

xxvi) α,ω-bis[3,4-epoxycyclohexylethanediyl-1,1,3,3-tetramethyldisiloxanyl-3,1-propanediyl]polytetrahydrofuran

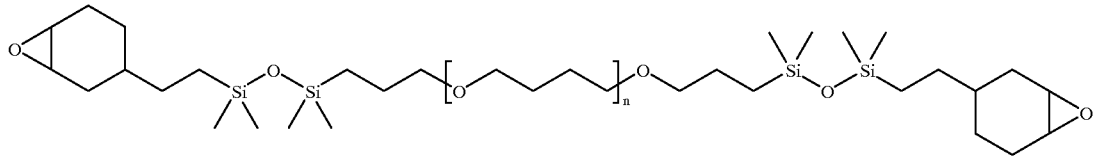

xxvii) α,ω-bis{3-oxatricyclo[3.2.1.0$^{2,4}$]octyl-6-carboxy}polytetrahydrofuran

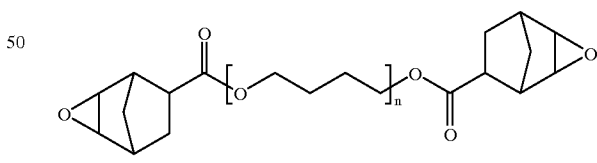

xxviii) α,ω-bis{3,8-dioxatricyclo[3.2.1.0$^{2,4}$]octyl-6-carboxy}polytetrahydrofuran

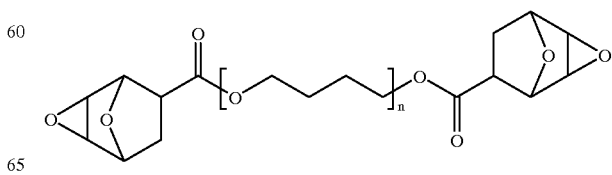

xxix) α,ω-bis(3-propanediyl-3,5,7-tris(2,1-ethanediyl-3,4-epoxycyclohexyl)-1,3,5,7-tetramethylcyclotetrasiloxanyl)polytetrahydrofuran

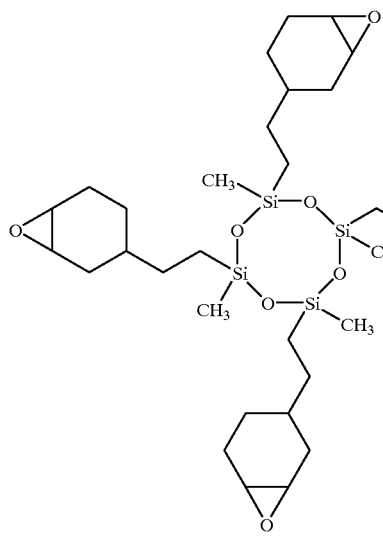
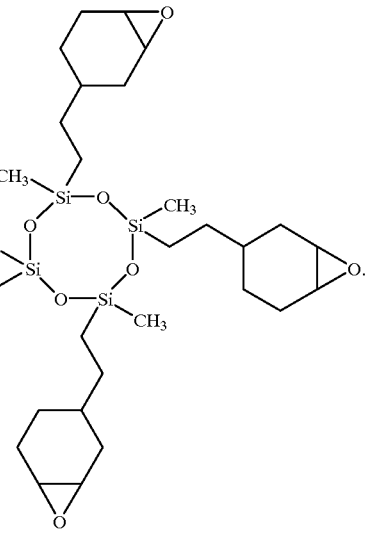

3. Polymerizable composition as claimed in patent claim 1, characterized in that it comprises, as the low-viscosity epoxide according to component b) 3,4-epoxycyclohexylmethyl 3,4-epoxycyclohexanecarboxylate, 3,4-epoxy-6-methylcyclohexyl 3,4-epoxy-6-methyl cyclohexanecarboxylate, dicyclopentadiene dioxide, bis(3,4-epoxycyclohexylmethyl)adipate, 1,3,5,7-tetrakis(2,1-ethanediyl-3,4-epoxycyclohexyl)-1,3,5,7-tetramethyl-cyclotetrasiloxane, 1,3,5,7,9-pentakis(2,1-ethanediyl-3,4-epoxycyclohexyl)-1,3,5,7,9-pentamethylcyclopentasiloxane, 1,1,3,3-tetramethyl-1,3-bis(ethanediyl-3,4-epoxycyclohexyl)disiloxane and/or low molecular weight siloxanes functionalized with cycloaliphatic epoxides.

4. Polymerizable composition according to at least one of patent claim 1, characterized in that it comprises, as fillers according to component c), quartz, ground glasses, silica gels or silicic acids or granules thereof.

5. Polymerizable composition according to at least one of patent claim 1, characterized in that it comprises, as retardants, accelerators and/or initiators, Lewis acids or Broensted acids or compounds from which such as acids are formed by irradiation with UV light or visible light or by heat and/or pressure.

6. Polymerizable composition according to at least one of patent claim 1, characterized in that it comprises, as auxiliaries, diols, diluents, stabilizers, inhibitors and/or pigments.

7. Polymerizable composition according to at least claim 1, comprising

A a paste comprising the epoxides of components (a) and (b), a portion or all of the filler of component (c), if appropriate retardants or accelerators according to component (d) and if appropriate auxiliaries of component (e), and, spatially separated therefrom, B a paste comprising an initiator according to component (d), if appropriate a portion of the filler of component (c) and if appropriate auxiliaries according to component (e).

8. The polymerizable dental composition of claim 1, wherein for type A, if n=2 and if Z denotes a cycloaliphatic, aromatic or alaphatic radical, then the radical has 1 to 18 carbon atoms.

9. The polymerizable dental composition of claim 1, wherein for type A, if n>2 and if Z denotes a cycloaliphatic, aromatic or alaphatic radical, then the radical has 1 to 18 carbon atoms.

10. The polymerizable dental composition of claim 1, wherein for type B, if Z denotes a cycloaliphatic, aromatic or alaphatic radical, then the radical has 1 to 18 carbon atoms.

11. An epoxide selected from the group consisting of:

i) 2,2-bis[4,1-phenylenoxy-3,1-propanediyl-3,4-epoxycyclohexylcarboxylic acid ester]propylidene

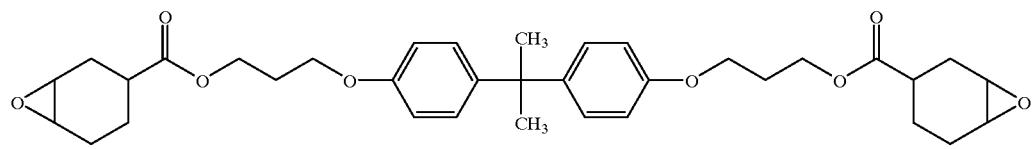

ii) 2,2-bis[4,1-phenylenoxy-3,1-propanediyl-oxy-methanediyl-3,4-epoxycyclohexyl]propylidene

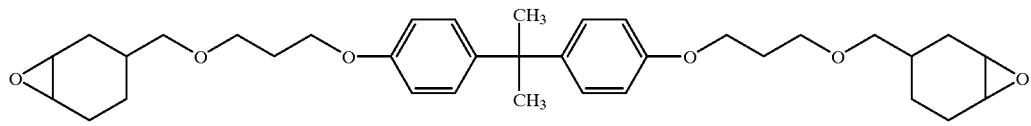

iii) 2,2-bis[3,4-epoxycyclohexylmethanediyl(4,1-phenylenoxy-3,1-propylcarboxylic acid ester)]propylidene

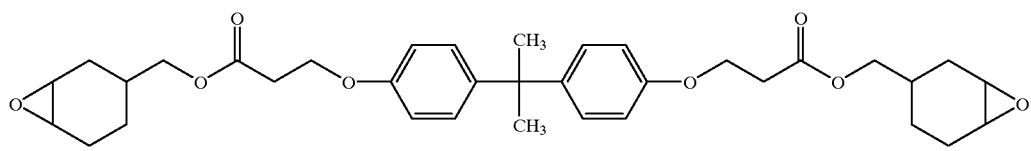

iv) 2,2-bis[4,1-phenylenoxy-3,1-propanediyl-1,1,3,3-tetramethyldisiloxanyl-1,2-ethanediyl-3,4-epoxycyclohexyl]propylidene

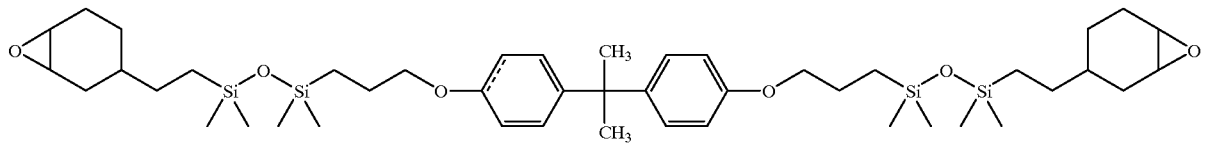

v) 2,2-bis{4,1-phenylenoxy-3,1-propanediyl-3-oxatricyclo[3.2.1.0$^{2,4}$]octyl-6-carboxy}propylidene

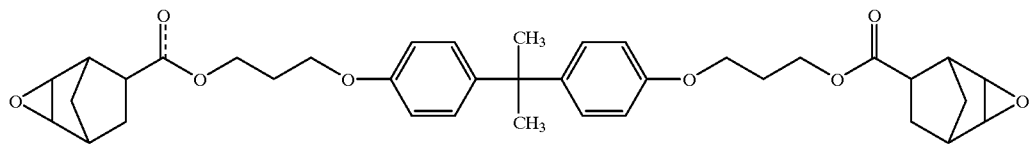

vi) 2,2-bis{4,1-phenylenoxy-3,1-propanediyl-3,8-dioxatricyclo[3.2.1.0$^{2,4}$]octyl-6-carboxy}propylidene

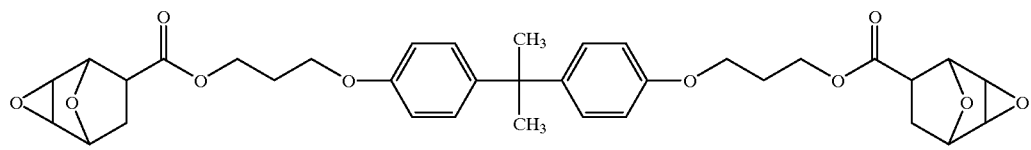

vii) 2,2-bis{4,1-phenylenoxy-3,1-propanediyl-[3,5,7-tris(ethanediyl-3,4-epoxycyclohexyl)-1,3,5,7-tetramethylcyclotetrasiloxanyl]}propylidene

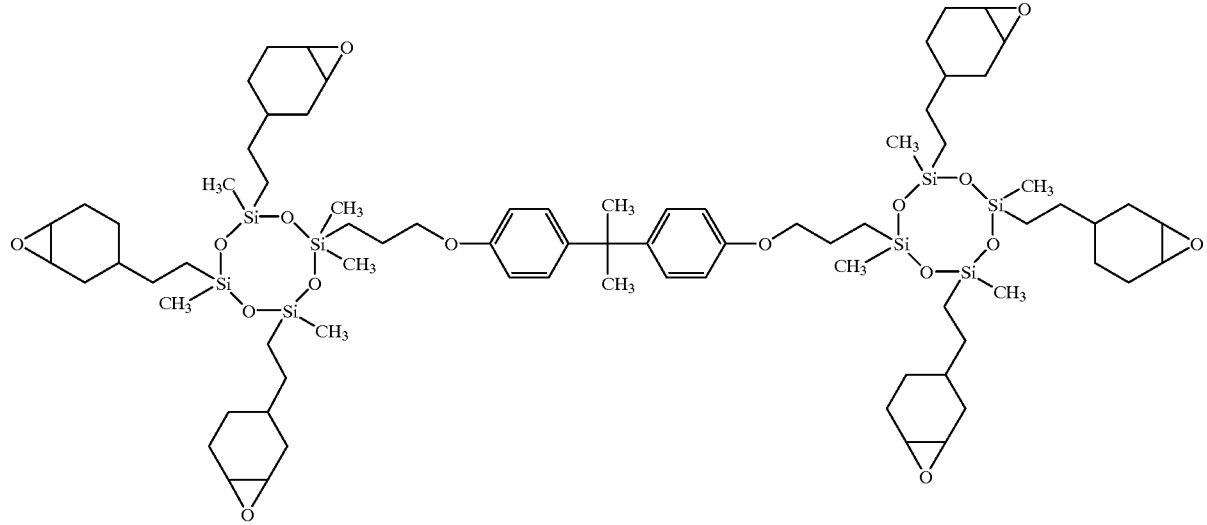

viii) bis[methanediyl-oxy-3,1-propanediyl-3,4-epoxycyclohexylcarboxylic acid ester]tricyclo[5.2.1.0$^{2,6}$]decane

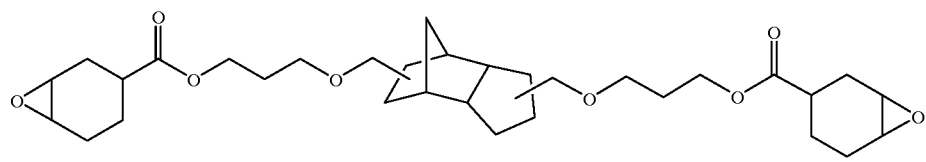

ix) bis[methanediyl-oxy-3,1-propanediyl-oxy-methanediyl-3,4-epoxycyclohexyl]tricyclo[5.2.1.0$^{2,6}$]decane

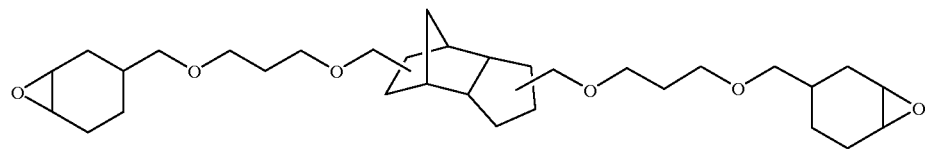

x) bis[3,4-epoxycyclohexylmethanediyl-propanecarboxylic acid-1-oxy-methanediyl]tricyclo[5.2.1.0$^{2,6}$]decane

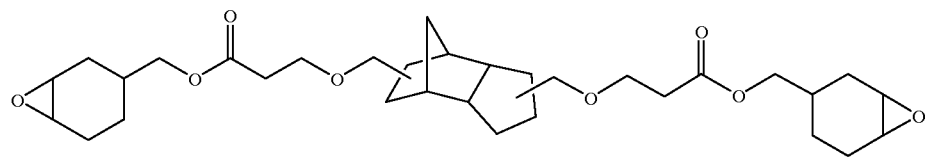

xi) bis(methanediyl-oxy-3,1-propanediyl-1,1,3,3-tetramethyldisiloxanediyl-1,2-ethanediyl-3,4-epoxycyclohexyl)tricyclo[5.2.1.0$^{2,6}$]decane

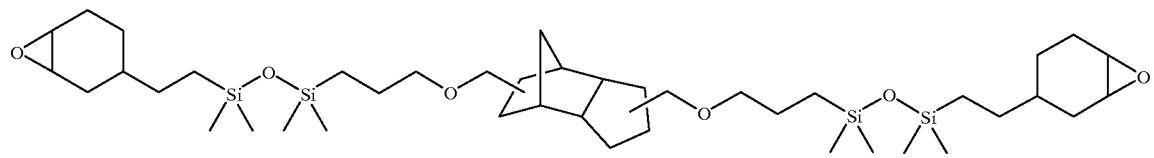

xii) bis{methanediyl-oxy-3,1-propanediyl-3-oxatricyclo[3.2.1.0$^{2,6}$]octyl-6-carboxyl}tricyclo[5.2.1.0$^{2,6}$]decane

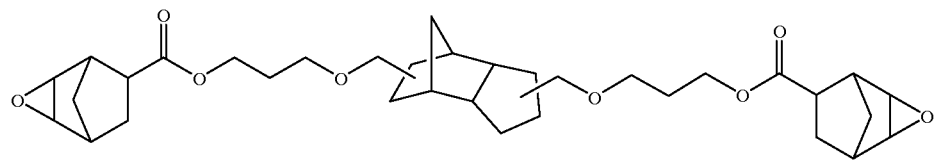

xiii) bis{methanediyl-oxy-3,1-propanediyl-3,8-dioxatricyclo[3.2.1.0$^{2,6}$]octyl-6-carboxyl}tricyclo[5.2.1.0$^{2,6}$]decane

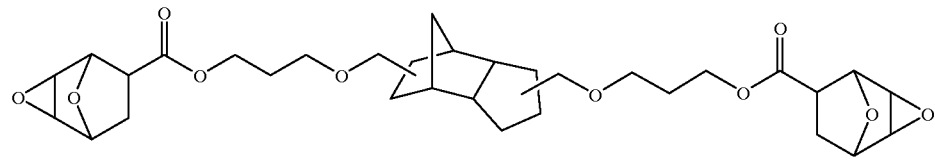

xiv) bis(methanediyl-oxy-(3-propanediyl-3,5,7-tris(2,1-ethanediyl-3,4-epoxycyclohexyl)-1,3,5,7-tetramethylcyclotetrasiloxanyl)-tricyclo[5.2.1.0$^{2,6}$]decane

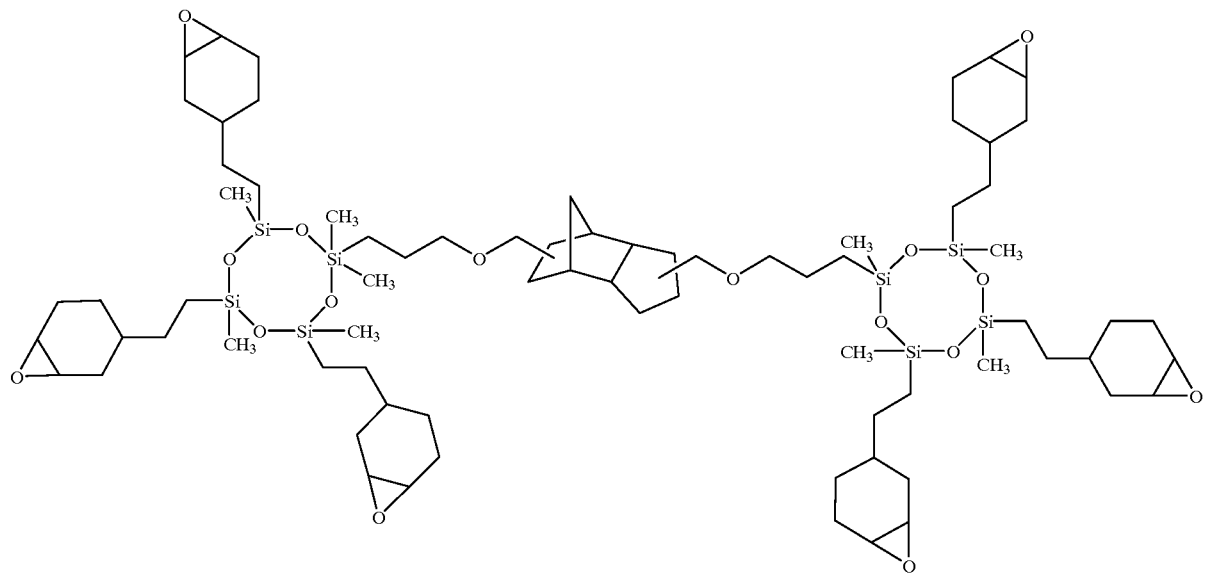

xv) 1,1,1-tris[methanediyl-oxy-methanediyl-3,4-epoxycyclohexyl]propane

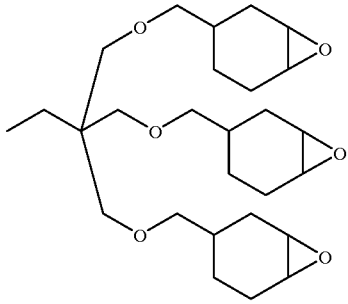

xvi) 1,1,1-tris[methanediyl-oxy-1,3-propanediyl-1,1,3,3-tetramethyldisiloxanediyl-1,2-ethanediyl-3,4-epoxycyclohexyl]propane

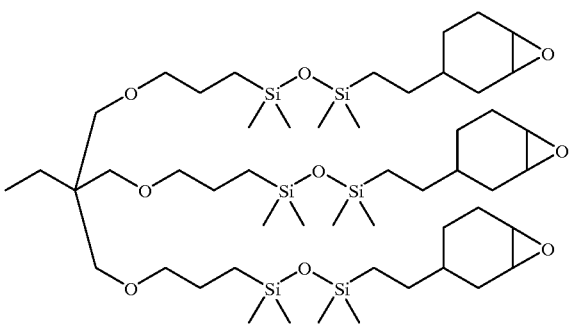

xvii) 1,1,1-tris{methanediyl-3-oxatricyclo[3.2.1.0$^{2,4}$]octyl-6-carboxy}propane

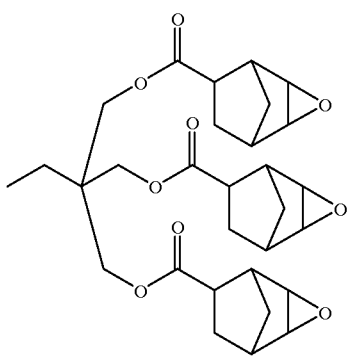

xviii) 1,1,1-tris{methanediyl-3,8-dioxatricyclo[3.2.1.0$^{2,4}$]octyl-6-carboxy}propane

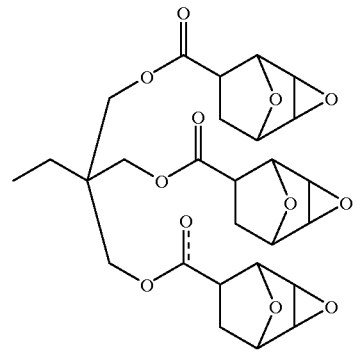

xix) 1,1,1-tris[methanediyl-oxy-3,1-propanediyl-3,5,7-tris(2,1-ethanediyl-3,4-epoxycyclohexyl)-1,3,5,7-tetramethylcyclotetrasiloxanyl]propane

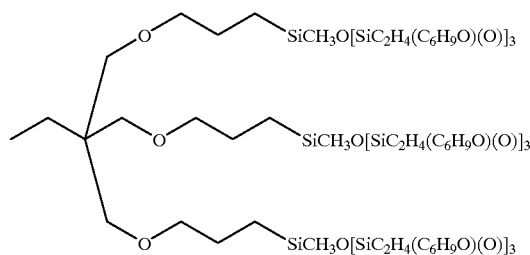

xx) 1,1,1-tris[methanediyl-oxy-bis(ethanedilyloxy)-3,4-epoxycyclohexylcarboxylic acid ester]propane

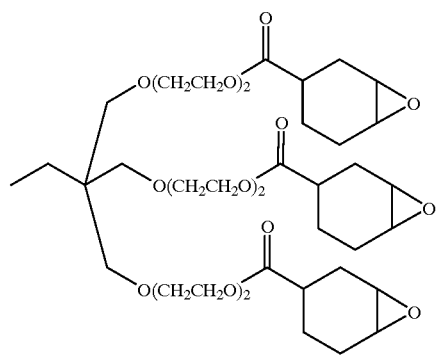

xxi) 1,1,1-tris[methanediyl-oxy-bis(ethanediyloxy)-methanediyl-3,4-epoxycyclohexyl]propane

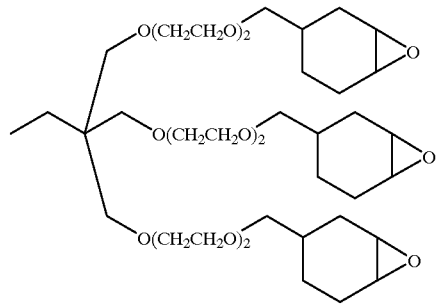

xxii) 1,1,1-tris[methanediyl-oxy-bis(ethanediyloxy)-propanediyl-1,1,3,3-tetramethyldisiloxanyl-1,2-ethanediyl-3,4-epoxycyclohexyl]propane

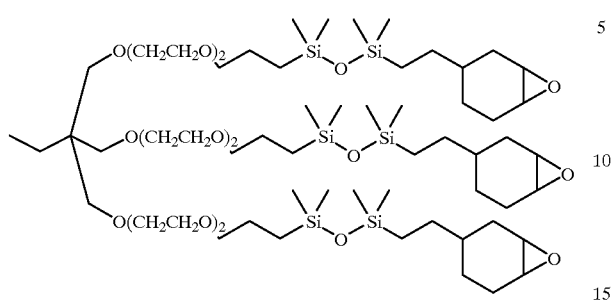

xxiii) 1,1,1-tris{methanediyl-oxy-bis(ethanediyloxy)-3-oxatricyclo[3.2.1.0$^{2,4}$]octyl-6-carboxy}propane

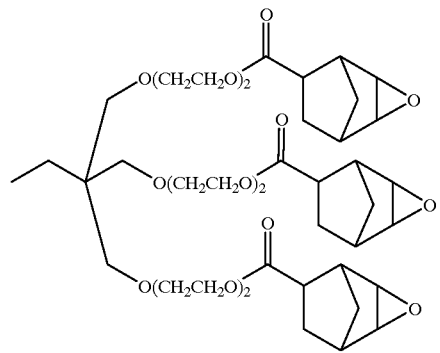

xxiv) 1,1,1-tris{methanediyl-oxy-bis(ethanediyloxy)-3,8-dioxatricyclo[3.2.1.0$^{2,4}$]octyl-6-carboxy}propane

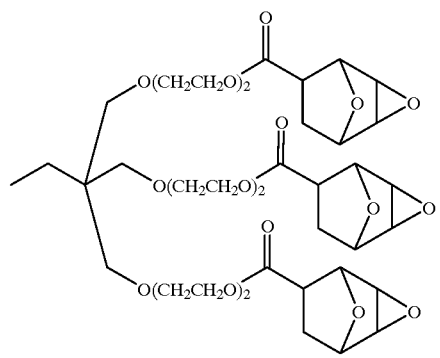

xxv) 1,1,1-tris[methanediyl-oxy-bis(ethanediyloxy)-propanediyl-3,5,7-tris(2,1-ethanediyl-3,4-epoxycyclohexyl)-1,3,5,7-tetramethylcyclo-tetrasiloxanyl]propane

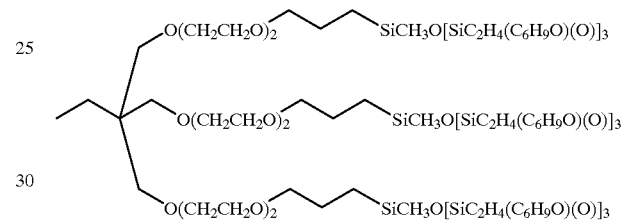

xxvi) α,ω-bis[3,4-epoxycyclohexylethanediyl-1,1,3,3-tetramethyldisiloxanyl-3,1-propanediyl] polytetrahydrofuran

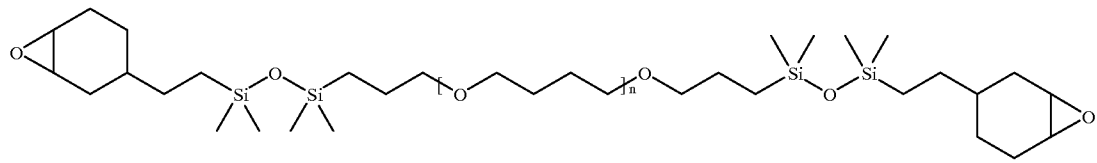

xxvii) α,ω-bis{3-oxatricyclo[3.2.1.0$^{2,4}$]octyl-6-carboxy}polytetrahydrofuran

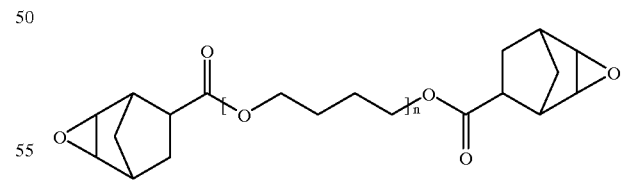

xxviii) α,ω-bis{3,8-dioxatricyclo[3.2.1.0$^{2,4}$]octyl-6-carboxy}polytetrahydrofuran

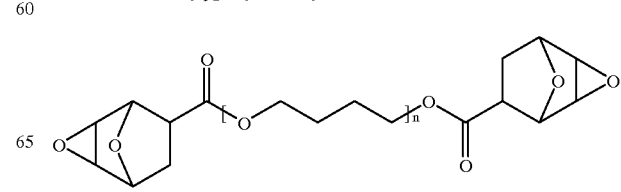

xxix) α,ω-bis(3-propanediyl-3,5,7-tris(2,1-ethanediyl-3,4-epoxycyclohexyl)-1,3,5,7-tetramethylcyclotetrasiloxanyl)polytetrahydrofuran
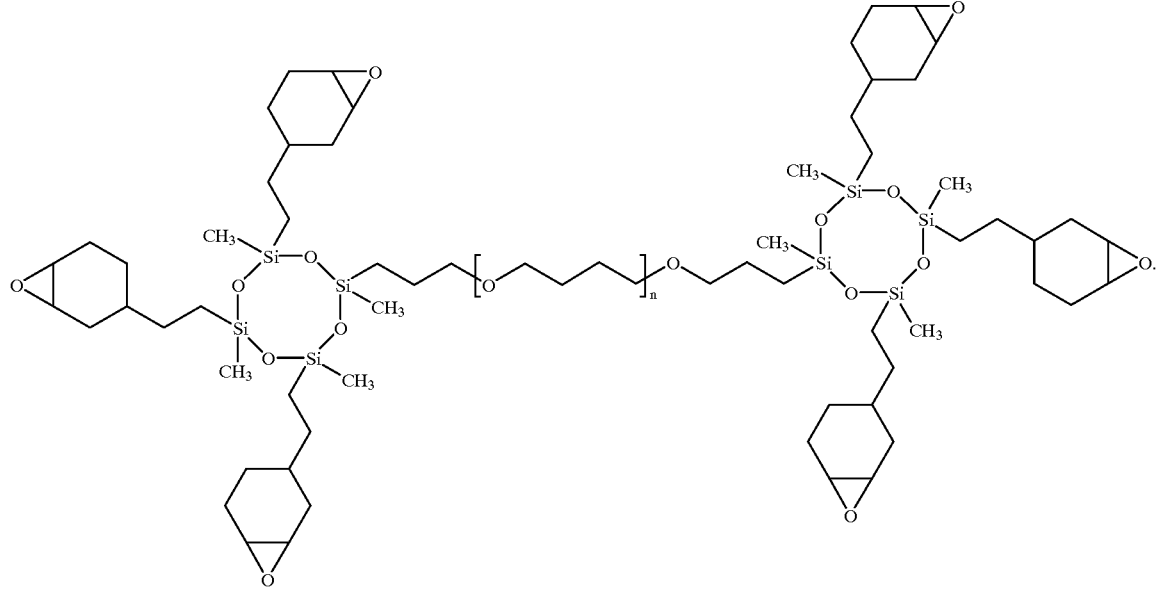
* * * * *